US008841137B2

(12) United States Patent
DeLouise et al.

(10) Patent No.: US 8,841,137 B2
(45) Date of Patent: Sep. 23, 2014

(54) HYBRID TARGET ANALYTE RESPONSIVE POLYMER SENSOR WITH OPTICAL AMPLIFICATION

(75) Inventors: Lisa DeLouise, Rochester, NY (US); Lisa Bonanno, Rochester, NY (US)

(73) Assignee: University of Rochester, Rochester, NY (US)

( * ) Notice: Subject to any disclaimer, the term of this patent is extended or adjusted under 35 U.S.C. 154(b) by 729 days.

(21) Appl. No.: 13/035,887

(22) Filed: Feb. 25, 2011

(65) Prior Publication Data
US 2011/0212463 A1     Sep. 1, 2011

Related U.S. Application Data

(60) Provisional application No. 61/308,242, filed on Feb. 25, 2010.

(51) Int. Cl.
*G01N 33/551* (2006.01)
*G01N 33/543* (2006.01)

(52) U.S. Cl.
CPC .. *G01N 338/54306* (2013.01); *G01N 33/54386* (2013.01); *Y10S 436/805* (2013.01)
USPC ............. 436/524; 385/12; 385/129; 385/130; 385/131; 422/82.11; 435/288.7; 436/164; 436/525; 436/805

(58) Field of Classification Search
None
See application file for complete search history.

(56) References Cited

U.S. PATENT DOCUMENTS 5,242,828 A  *  9/1993  Bergstrom et al.  ........  435/287.1
5,436,161 A  *  7/1995  Bergstrom et al.  ...........  422/425
6,514,689 B2       2/2003  Han et al.
6,835,553 B2      12/2004  Han et al.
2008/0275318 A1 * 11/2008  Lastovich et al.  .............  600/316

OTHER PUBLICATIONS

Bonanno & Delouise, "Design of a Hybrid Amine Functionalized Polyacrylamide Hydrogel—Porous Silicon Optical Sensor," Proc. SPIE 7167:71670E-1-71670E-11 (2009).
Bonanno & Delouise, "Integration of a Chemical-Responsive Hydrogel into a Porous Silicon Photonic Sensor for Visual Colorimetric Readout," Adv. Funct. Mater. 20:573-78 (2010).
Bonanno & Delouise, "Optical Detection of Polyacrylamide Swelling Behavior in a Porous Silicon Sensor," Mater. Res. Soc'y Symp. Proc. 1133:AA01-05 (2008).
Bonanno & Delouise, "Tunable Detection Sensitivity of Opiates in Urine via a Label-Free Porous Silicon Competitive Inhibition Immunosensor," Anal. Chem. 82(2):714-22 (2010).
Bonanno & Delouise, "Whole Blood Optical Biosensor," Biosens. Bioelectron. 23:444-48 (2007).
Bonanno et al., "Hybrid Nanoporous Silicon Optical Biosensor Architectures for Biological Sample Analysis," Proc. SPIE, 7553:75530L-1-75530L-8 (2010).

(Continued)

*Primary Examiner* — Chris L Chin
(74) *Attorney, Agent, or Firm* — LeClairRyan, a Professional Corporation

(57) ABSTRACT

Disclosed is a product that includes an optical sensor; a target-responsive hydrogel matrix on a surface of the optical sensor (where the hydrogel matrix comprises one or more target-specific receptors and one or more target analogs), and one or more high refractive index nanoparticles within the hydrogel matrix, where a detectable change occurs in a refractive index of the hydrogel matrix when contacted with one or more target molecules. Sterile packages and detection devices containing the product, and methods of detecting a target molecule using the product, are also disclosed.

44 Claims, 10 Drawing Sheets

(56) References Cited

OTHER PUBLICATIONS

Endo et al., "Stimuli-Responsive Hydrogel—Silver Nanoparticles Composite for Development of Localized Surface Plasmon Resonance-Based Optical Biosensor," Anal. Chim. Acta 611:205-11 (2008).
Jane et al., "Porous Silicon Biosensors on the Advance," Trends Biotech. 27(4):230-39 (2009).
Kilian et al., "Peptide-Modified Optical Filters for Detecting Protease Activity," ACS Nano 1(4):355-61 (2007).
Lei et al., "Integration of Hydrogels with Hard and Soft Microstructures," J. Nanosci. Nanotech. 7:780-89 (2007).
Orosco et al., "Protein-Coated Porous-Silicon Photonic Crystals for Amplified Optical Detection of Protease Activity," Adv. Mater. 18:1393-96 (2006).
Sailor, "Color Me Sensitive: Amplification and Discrimination in Photonic Silicon Nanostructures," ACS Nano 1 (4):248-52 (2007).
Stein Em et al., "DNA Hybridization-Enhanced Porous Silicon Corrosion: Mechanistic Investigations and Prospect for Optical Interferometric Biosensing," Tetrahedron 60:11259-67 (2004).
Voelcker et al., "Catalyzed Oxidative Corrosion of Porous Silicon Used as an Optical Transducer for Ligand—Receptor Interactions," ChemBioChem 9:1776-86 (2008).
Zhang et al., "Recent Advances in Nanotechnology Applied to Biosensors," Sensors 9:1033-53 (2009).

\* cited by examiner

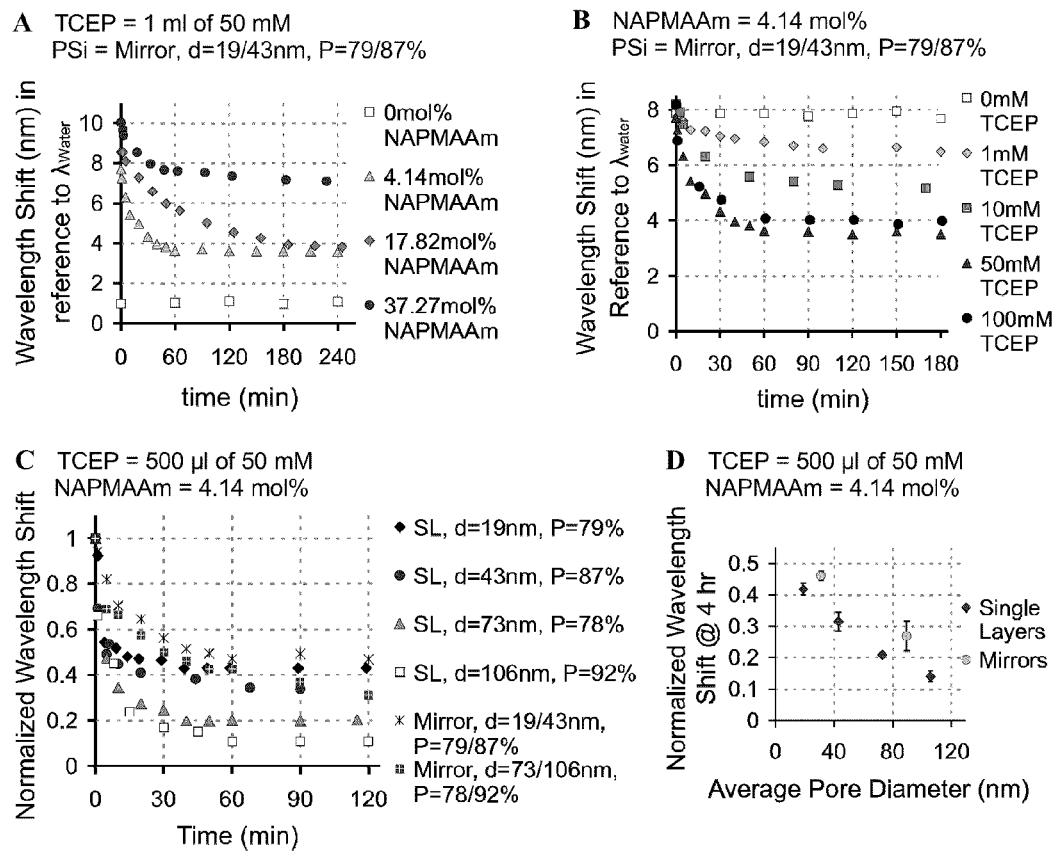
Figures 4A–D
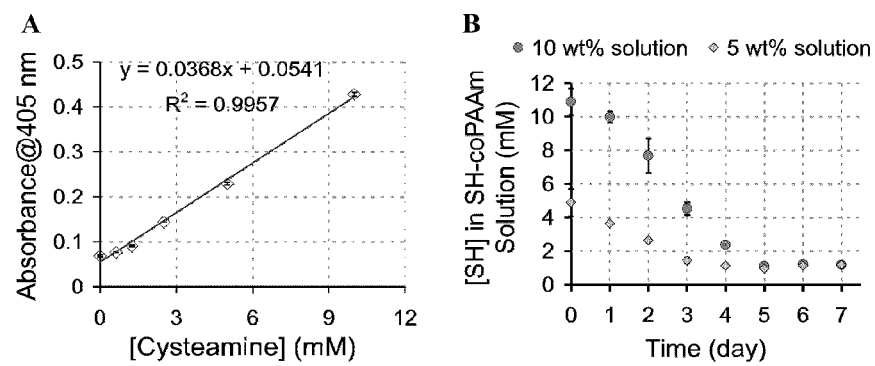
Figures 5A–B

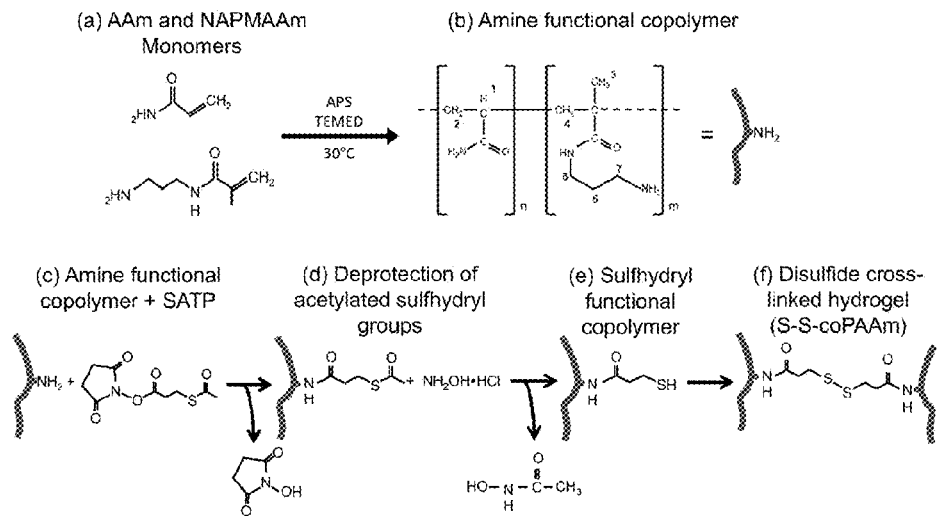
Figures 6A–F
| mol% NAPMAAm: | 37.4 | 17.8 | 4.14 | 0 |
|---|---|---|---|---|
| Initial bulk hydrogel | | | | |
| 0.1 nmol TCEP, 15 min | | | | |
| 1 nmol TCEP, 15 min | | | | |
| 100 nmol TCEP, 15 min | | | | |
Figure 7
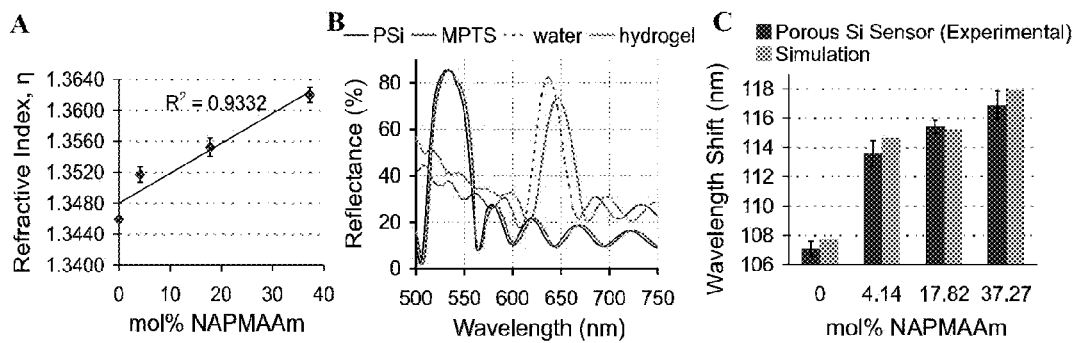
Figures 8A–C

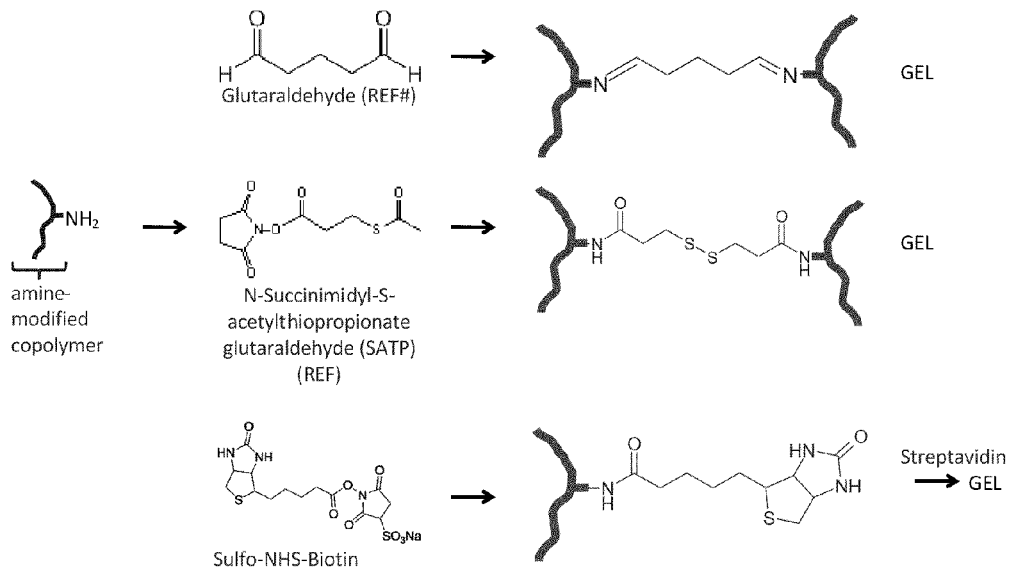
Figure 11
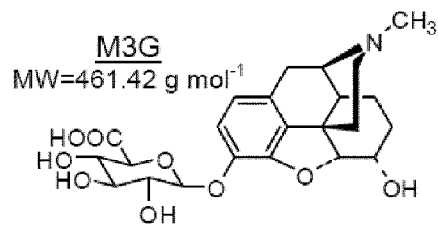
Figure 12
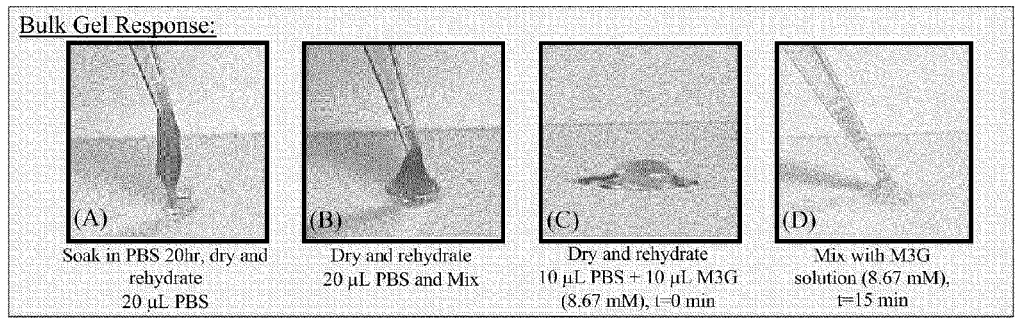
Figures 13A–D

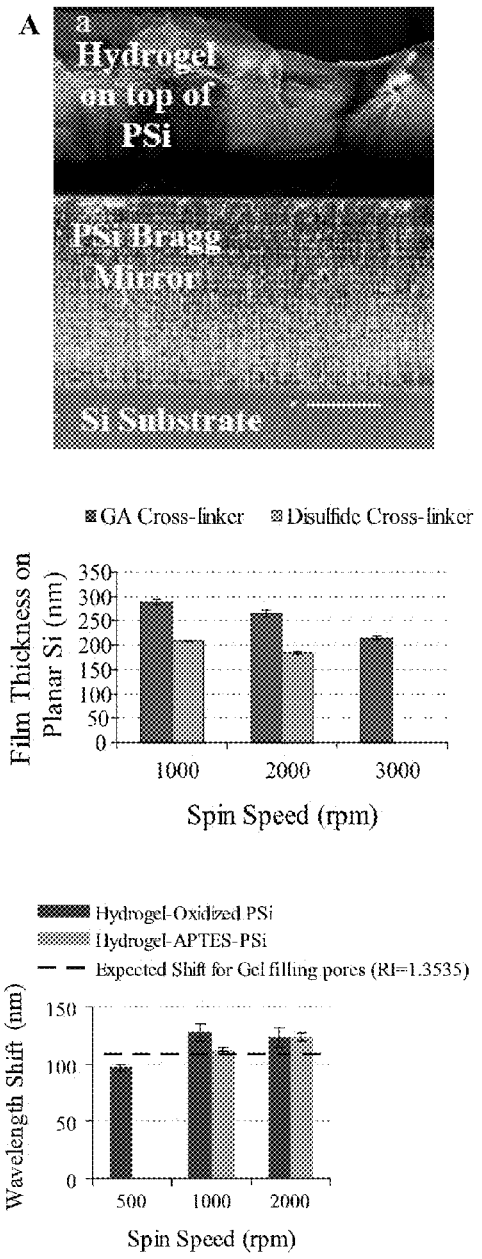
Figures 15A–C

HYBRID TARGET ANALYTE RESPONSIVE POLYMER SENSOR WITH OPTICAL AMPLIFICATION

This application claims the benefit of U.S. Provisional Patent Application Ser. No. 61/308,242, filed Feb. 25, 2010, which is hereby incorporated by reference in its entirety.

The invention was made with government support under Grant No. 5K25AI060884 awarded by National Institutes of Health/National Institute of Allergy and Infectious Diseases and Grant Nos. T32DA007232 and F31DA025398 awarded by National Institutes of Health/National Institute on Drug Abuse. The U.S. Government has certain rights.

FIELD OF THE INVENTION

The present invention relates generally to hybrid target analyte responsive polymer sensors that include high refractive index nanoparticles, as well as methods of making and using these sensors.

BACKGROUND OF THE INVENTION

The increasing need for rapid and portable biosensor technology is evidenced by the growing worldwide markets for environmental field testing (FT) (GERSHON J. SHUGAR ET AL., ENVIRONMENTAL FIELD TESTING AND ANALYSIS READY REFERENCE HANDBOOK (2001)) and point-of-care (POC) biomedical diagnostics markets (Kalorama Information, "World Markets for Point of Care Diagnostics," 13 (2009)), the latter with obvious applications in home health testing (e.g. cholesterol, pregnancy), drugs of abuse screening (e.g. sporting venues, clinic, sobriety check points), and pathogen surveillance for military, homeland security and public health testing. A successful FT/POC platform technology will, in addition to speed, sensitivity and accuracy, be inexpensive and not require extensive training or sophisticated instrumentation for readout. It would utilize a signal transduction strategy that readily extends to the detection of a wide range of targets for which the concentration level that triggers a positive response is tunable for a screening assay and has a wide dynamic range and high target specificity for a quantitative assay. Immunochromatographic test strips comprise many of the commercially-available rapid diagnostics. Signal transduction is based on lateral flow technology that couples a target antibody to a colorimetric agent such as gold nanoparticles which are drawn over capture and control zones by capillary action. Lateral flow devices produce signals detectable by eye but suffer sensitivity and reliability issues and studies indicate that, while simple and rapid, they produce less than acceptable results for wide clinical acceptance (Ferris & Martin, *J. Fam. Pract.* 34:593-97 (1992); Hook et al., *JAMA* 272:867-70 (1994); Kluytmans et al., *J. Clin. Microbiol.* 31:3204-10 (1993)).

In recent years innovation in FT/POC technology development has focused on label free sensors exploiting the unique optical and electrical properties of nanomaterials (Wang et al., *Mater. Today* 8(5):20-31 (2005); Jain, *Clin. Chim. Acta* 358(1/2):37-54 (2005)). One such material, electrochemically synthesized porous silicon (PSi) (Bonanno & DeLouise, *Anal. Chem.* 82:714-22 (2010), holds great promise for FT/POC sensor development. PSi is prepared by anodic electrochemical dissolution of a single crystal silicon wafer in an electrolyte containing hydrofluoric acid (HF) (Jane et al., *Trends Biotech.* 27:230-39 (2009); Sailor, *ACS Nano* 1(4): 248-52 (2007); DeLouise & Miller, *Proc. SPIE* 5357:111-25 (2004); Vinegoni et al., "Porous Silicon Microcavities," in 2 SILICON-BASED MATERIALS AND DEVICES 122-88 (Hari Nalwa ed., 2001)). Etch parameters can be tuned to achieve a high degree of control over pore diameter (10-150 nm) and porosity (20-90%) which are essential properties for fabrication of photonic structures for biosensing applications as they dictate the optical and signal transduction properties and device sensitivity.

There are many advantages of PSi technology for FT/POC sensing applications including inexpensive fabrication, precise control of pore morphology (pore diameter and porosity), intrinsic filtering properties (molecular size selection), high surface area (>100 $m^2/g$), versatile surface chemistry, capacity for label-free colorimetric readout, and compatibility with high throughput array and microfluidic technologies (Bonanno & DeLouise, *Anal Chem.* 82:714-22 (2010); Sailor, *ACS Nano* 1(4):248-52 (2007); Jane et al., *Trends Biotech.* 27(4): 230-39 (2009); Bonanno & DeLouise, *Biosens. Bioelect.* 23:444-48 (2007)). Many proof of principle PSi sensors have been demonstrated for detecting proteins (Ouyang et al., *Anal. Chem.* 79(4):1502-06 (2007); DeLouise & Miller, *Mater. Res. Soc. Symp. Proc.* 782:A5.3.1 (2004)), oligonucleotides (Rong et al., *Biosens. Bioelect.* 23(10):1572-76 (2008); Di Francia et al., *Biosens. Bioelect.* 21(4):661-65 (2005); Steinem et al., *Tetrahedron* 60:11259-67 (2004)), enzymes (Kilian et al., *ACS Nano* 1(4):355-61 (2007); DeLouise & Miller, *Anal. Chem.* 77(10):3222-30 (2005); DeLouise & Miller, *Anal. Chem.* 77(7):1950-56 (2005); Orosco et al., *Adv. Mater.* 18(11):1393-96 (2006)), small molecules (Bonanno & DeLouise, *Anal. Chem.* 82:714-22 (2010); Lin et al., *Biosensor Sci.* 278(5339):840 (1997)), and gases (Pancheri et al., *Sens. Actuators B* 89:237 (2003)). However, little effort has focused on the translation of PSi devices for FT/POC clinical use.

The bio sensor signal transduction principle is based on measurement of refractive index ($\eta$) changes. The $\eta$ of a PSi layer depends on porosity which can be varied precisely between $\eta$=3.6 (bulk silicon, 0% porosity), to $\eta$=1 (air, 100% porosity). Optical devices (mirrors, microcavities, and rugate filters) are fabricated by etching multilayer structures with alternating porosity (Jane et al., *Trends Biotech.* 27:230-39 (2009)). These structures function as label-free optical sensors by reporting changes in $\eta$ (porosity) that result when target binds immobilized receptors. Target binding causes a change in porosity and consequently a change in refractive index ($\eta$) that is monitored as a shift in the color of reflected light (i.e., wavelength shift, $\Delta\lambda r$) from the sensor. The magnitude of $\Delta\lambda r$ is a function of the thickness (amount) of the bound material and its refractive index. Target binding decreases porosity, which increases $\eta$, causing a red shift in the optical spectrum.

The magnitude of the optical shift has been shown to be a linear function of pore filling (DeLouise & Miller, *Proc. SPIE* 5357:111-25 (2004)). Wavelength shift sensitivity (WSS) is a figure of merit specific to each sensor and is measured by displacing air in the pores with liquids of varying refractive index. The WSS value is the slope of the plot of wavelength shift magnitude vs. $\eta$. For typical sensors, the WSS values range between 200-400 nm/RIU (DeLouise & Miller, *Mater. Res. Soc'y Symp. Proc.* 782:A5.3.1 (2003); DeLouise & Miller, *Anal. Chem.* 77(10):3222-30 (2005); DeLouise & Miller, *Proc. SPIE* 5357:111-25 (2004)), which translates to detecting a ~$10^{-3}$ to $10^{-4}$ change in refractive index. This enables target detection sensitivity ranging from mg/ml (Bonanno & DeLouise, *Biosens. Bioelect.* 23:444-48 (2007) to µg/ml (Dancil et al., *J. Am. Chem. Soc'y* 121:7925-30 (1999)) or pg/$mm^2$ (DeLouise & Miller, *Anal. Chem.* 77(10):3222-30 (2005); Lin et al., *Science* 278:840-43 (1997)) or nM (Kilian et al., *ACS Nano* 1(4):355-61 (2007)) depending upon the receptor/target system and the assay protocol used (Sailor, *ACS Nano* 1(4):248-52 (2007); Jane et al., *Trends Biotech.* 27(4):230-39 (2009)). A much higher limit of detection is desired (picomolar or ng/ml) but this has not yet been achieved with PSi technology. Novel optical signal amplification strategies to increase detection sensitivity and to achieve colorimetric read out by eye would be advantageous.

Devising a strategy to achieve these goals must take into consideration the unique characteristics of the PSi transducer. First, because signal transduction occurs within the porous matrix, the sensor architecture and assay protocol must be designed to overcome the effects of pore blocking, steric crowding, and baseline drift. Baseline drift in the PSi optical response can result from either corrosion of the sensor or from nonspecific adsorption of substances present in complex biological samples (Dancil et al., *J. Am. Chem. Soc'y* 121:7925-30 (1999); Lees et al., *Langmuir* 19(23):9812-17 (2003); Canham et al., *Physica Status Solidi (A)* 182:521 (2000)). Methods to prevent baseline drift are well developed and involve passivating the PSi surface with Si—O or Si—C bond formation (thermal oxidation or hydrosilylation) and utilizing appropriate blocking chemistries and washing protocols (Buriak & Allen, *J. Am. Chem. Soc'y* 120:1339-40 (1998); Kilian et al., *Chem. Commun.* 14(6):630-40 (2009); Boukheroub et al., *J. Electrochem. Soc'y* 149:59-63 (2002); Canham et al., *Adv. Mater.* 11:1505-09 (1999)). Pore blocking and steric crowding effects are also well understood and can be overcome by tuning the pore diameter and optimizing the surface receptor concentration (DeLouise & Miller, *Mater. Res. Soc'y Symp. Proc.* 782:A5.3.1 (2003); Bonanno & DeLouise, *Langmuir* 23:5817-23 (2007)). The latter, unfortunately, may limit the ability to take advantage of the enormous internal surface area of PSi to immobilize a high receptor concentration. Strategies to attain optical signal amplification for improving the limit of detection and colorimetric readout by eye are less developed and constitute an active area of research in the PSi sensor field (Kilian et al., *ACS Nano* 1(4):355-61 (2007); Orosco et al., *Adv. Mater.* 18(11):1393-96 (2006); Bonanno & DeLouise, *Adv. Funct'l Mater.* 20(4):573-78 (2010)).

In traditional bioassay design, signal amplification is commonly achieved using fluorescent or enzymatic secondary reporters (ELISA, PCR). The coupling of enzymatic and/or catalytic reactions to biosensor signal generation is a growing trend (Jane et al., *Trends Biotech.* 27(4):230-39 (2009); Wang & Lin, *Trends Analyt. Chem.* 27 (7):619-26 (2008); Jensen & Torabi, *J. Optical Soc'y Am. B: Opt. Phys.* 3(6):857-63 (1986)). While effective, these methods add significant cost and assay time that label-free technologies seek to overcome for POC applications. Sailor and coworkers have recently demonstrated clever extrapolations of enzymatic signal generation to enhance detection sensitivity of proteases in PSi sensors (Orosco et al., *Adv. Mater.* 18(11):1393-96 (2006)). In this work a protein layer is coated over a PSi sensor. Protease activity was then detected by measuring optical red shifts (increase in refractive index) due to small peptide fragments (~7 mM) of the digested protein layer infiltrating the PSi pores. This was followed by the work of Gooding and coworkers (Kilian et al., *ACS Nano* 1(4):355-61 (2007)) who embedded protein within the PSi matrix and optically detected protease activity (37 nM) by monitoring a blue shift (decreases in refractive index) resulting from protein cleavage and peptide diffusion out of the sensor matrix. These approaches are unfortunately limited to detection of a generic class of enzymes. To overcome these limitations, Voelcker and coworkers have pioneered a label-free optical signal amplification strategy based on inducing PSi corrosion (Steinem et al., *Tetrahedron* 60:11259-67 (2004); Voelcker et al., *Chem Bio Chem.* 9:1776-86 (2008)). Formation of a duplex during DNA detection was found to trigger oxidative corrosion of the PSi substrate causing an irreversible increase in porosity and pore size and a profound decrease in refractive index (Steinem et al., *Tetrahedron* 60:11259-67 (2004)). Detection of DNA at 0.1 amol/mm$^2$ was achieved by this method. This serendipitous effect was later rationally extended by systematically identifying a transition metal complex that could catalyze PSi oxidation. A nickel(II)cyclam derivative was developed as a catalyst label and integrated into a detection assay to achieve amplified detection of biomolecules at submicromolar concentrations (Voelcker et al., *Chem Bio Chem.* 9:1776-86 (2008)). While this approach is still under development, the irreversible oxidative corrosion of the transducer may prove difficult to control and versatility in target has yet to be demonstrated. While constituting significant advancements, the above mentioned amplification strategies do not directly exploit the fact that the PSi is a volume (porosity) sensitive transducer.

Additionally, clinical and POC diagnostic devices require the specific detection of biological and/or chemical targets at low concentration, in an inexpensive, convenient, reliable, and rapid manner. Many innovative approaches have been reported to address this complex problem yet a need still exists for practical technology solutions. Responsive hydrogels that undergo morphological changes resulting from external stimuli have displayed great promise in chemical sensing (Holtz & Asher, *Nature* 389:829-32 (1997)) and medical diagnostics (Lapeyre et al., *Biomacromolecules* 7:3356-63 (2006); Kim et al., *Angew. Chem. Int'l Ed.* 45:1446-49 (2006); Miyata et al., *Nature* 399:766-69 (1999)) as well as drug delivery (Kiser et al., *Nature* 394:459-62 (1998)), tissue engineering (Lutolf et al., *Proc. Nat'l Acad. Sci. USA* 100:5413-18 (2003)), and microfluidic applications (Yu et al., *Appl. Phys. Lett.* 78:2589-91 (2001)). Variation of polymer composition, structure, and incorporation of specific functional groups have been exploited to develop hydrogels that respond to an array of biochemical targets including antigen (Yu et al., *Appl. Phys. Lett.* 78:2589-91 (2001)), DNA (Murakami & Maeda, *Biomacromolecules* 6:2927-29 (2005)), toxins (Frisk et al., *Chem. Mater.* 19:5842-44 (2007)), drugs (Ehrbar et al., *Nat. Mater.* 7:800-04 (2008)), and enzymes (Thornton et al., *Chem. Commun. (Camb)* 47:5913-15 (2005)). Integration of these smart polymers into specifically engineered sensing systems constitutes an active area of research.

Miniaturization of hydrogel dimensions facilitates reduced response times relative to bulk gel kinetics as required particularly for POC diagnostic testing (Lei et al., *Langmuir* 20:8947-51 (2004)). Notable success in development of smart hydrogel microlenses into multiplexed stimuli-sensor arrays has been achieved with response time of seconds (Kim et al., *Biomacromolecules* 8:1157-61 (2007); Dong et al., *Nature* 442:551-54 (2006)). However, reliance on optical instrumentation to monitor the responses from these microscale devices (change in refractive index or lens radius of curvature) is a drawback for POC applications.

A more attractive approach for POC applications is to integrate smart hydrogels with colloidal crystal arrays (Holtz & Asher, *Nature* 389:829-32 (1997); Lapeyre et al., *Biomacromolecules* 7:3356-63 (2006)) or photonic bandgap materials (Segal et al., *Adv. Funct'l Mater.* 17:1153-62 (2007)). These composite materials potentially enable direct optical detection of hydrogel morphological changes with rapid steady state response times of seconds to minutes.

Porous silicon (PSi) is a photonic material that is ideally suited for this application due to its inexpensive fabrication, robust optical transduction, and ease in translation for high-throughput analysis (Chan et al., *J. Am. Chem. Soc'y* 123:11797-98 (2001); Lin et al., *Science* 278:840-43 (1997); Bonanno & DeLouise, *Biosens. Bioelectron.* 23:444-48 (2007); Cunin et al., *Nat. Mater.* 1:39-41 (2002)). The unique capability of the PSi transducer to report refractive index ($\eta$) change that occur within the porous matrix can be exploited to detect target molecules binding directly to the PSi surface or optical changes that occur to a target-responsive gel incorporated into the porous matrix. Chemical and biological sensors have been developed to specifically capture target molecules onto the porous surface area to analyze complex samples in high-throughput and multiplexed assays (Chan et al., *J. Am. Chem. Soc'y* 123:11797-98 (2001); Lin et al., *Science* 278:840-43 (1997); Bonanno & DeLouise, *Biosens. Bioelectron.* 23:444-48 (2007); Cunin et al., *Nat. Mater.* 1:39-41 (2002)). In addition, visual color readout has been achieved in the detection of protease activity (Orosco et al., *Adv. Mater.* 18:1393-96 (2006); Gao et al., *Anal. Chem.* 80:1468-73 (2008)). Protease digestion of a protein layer coated on top of a PSi photonic crystal caused cleavage products to infiltrate the pores producing a large $\eta$ change that was observed by eye as a color change. These studies highlight the potential for developing PSi photonic sensors for POC diagnostic applications. The capability to easily tune the optical spectrum of the PSi-based 1-D photonic crystal during fabrication facilitates a more deterministic color change combination for portable POC sensing applications. For example, design of a green-to-red color change may be more readily interpreted than a sensor that results in a red-to-deeper-red or blue-to-green color change.

Hydrogel-supported PSi sensors have also been investigated (Segal et al., *Adv. Funct'l Mater.* 17:1153-62 (2007); DeLouise et al., *Adv. Mater.* 17:2199-203 (2005); Bonanno & DeLouise, *Mater. Res. Soc'y Symp. Proc.* 1133:AA01-05 (2008); Bonanno & DeLouise, *Proc. SPIE* 7167:71670F (2009)). Results show that the sensor maintains the capability to detect small changes in $\eta$ ($10^{-3}$-$10^{-4}$) that result from diffusion of small analytes (DeLouise et al., *Adv. Mater.* 17:2199-203 (2005)). Composite hydrogel-PSi sensors are also able to detect gel structural changes induced in response to stimuli (temperature and pH) (Segal et al., *Adv. Funct'l Mater.* 17:1153-62 (2007)) or that result from changes in gel composition (Bonanno & DeLouise, *Mater. Res. Soc'y Symp. Proc.* 1133:AA01-05 (2008); Bonanno & DeLouise, *Proc. SPIE* 7167:71670F (2009)). However, incorporation of a bio or chemo responsive hydrogel into a photonic PSi sensor with a tunable target response remains to be demonstrated.

The present invention is directed to overcoming these and other deficiencies in the art.

SUMMARY OF THE INVENTION

A first aspect of the present invention relates to a product comprising: an optical sensor; a target-responsive polymer matrix on a surface of the optical sensor, wherein the polymer matrix comprises one or more target-specific receptors and one or more target analogs; and one or more high refractive index nanoparticles within the polymer matrix; wherein a detectable change occurs in a refractive index of the polymer matrix when contacted with one or more target molecules.

A second aspect of the present invention relates to a method of detecting a target molecule comprising exposing a product described herein to a sample under conditions effective to allow binding of a target molecule in the sample to the one or more receptors; and determining whether a change in refractive index of the polymer matrix occurs following said exposing, whereby a change in refractive index indicates the presence of the target molecule in the sample.

The products of the invention provide a favorable aqueous environment for molecular-level interactions to occur (Zhang, *Nat. Mater.* 3(1):7-8 (2004), which is hereby incorporated by reference in its entirety), and increase the number of receptor sites over what can be immobilized onto a planar surface (Charles et al., *Biosens. Bioelect.* 20(4):753-64 (2004), which is hereby incorporated by reference in its entirety) by dispersing them throughout the PSi sensor volume. This also overcomes problems of receptor steric crowding limitations that arise in surface immobilization (Bonanno & DeLouise, *Langmuir* 23:5817-23 (2007), which is hereby incorporated by reference in its entirety). The products of the invention are ideally suited for detection of small molecular weight targets which pose difficulties to detect directly using label-free optical transducers because of the small refractive index changes they induce upon capture (Wang et al., *Electrochem. Commun.* 9(2):343-47 (2007), which is hereby incorporated by reference in its entirety). Because target specificity is determined foremost by the bioactive cross-linker and its differential binding affinity towards target and target analog, this constitutes a versatile sensor platform capable of detecting a wide range of bio/chemical targets.

BRIEF DESCRIPTION OF THE DRAWINGS

FIGS. 4A-D relate to the temporal optical detection of TCEP-responsive S—S-coPAAm hydrogel dissolution by wet PSi sensor reflectance spectrometry measurements taken with varying three design parameters: S—S-coPAAm hydrogel cross-linking density varied by adjusting mol % NAPMAAm (0-37.27 mol %) (FIG. 4A); varied outside concentration of TCEP (500 µl of 0-100 mM) (FIG. 4B); and varied PSi pore diameter and architecture (19-106 nm diameter single layer pores, all having thickness of 1.68 µm; and Bragg mirrors with alternating 19/43 and 73/106 nm diameter pores having thicknesses of 3.2 and 2.8 µm, respectively) (FIG. 4C). FIG. 4D is a graph of the normalized wavelength shift at 4 hours relative to the average pore diameter. Dissolution was dependent on the average pore diameter of the PSi substrate. d=diameter; P=porosity; SL=single layer.

FIGS. 5A-B relate to Ellman colorimetric assay detection of sulfhydryl groups. FIG. 5A is a standard curve created to identify absorbance intensity values at 405 nm for varying amounts of free sulfhydryl groups. Each mol of Cysteamine contains 1 mol of free sulfhydryl groups. FIG. 5B is a graph of the amount of sulfhydryl groups present in sulfhydryl functional copolymer solutions (4.14 mol % NAPMAAm) of 5 and 10 wt % in water monitored by Ellman's Assay.

FIGS. 6A-F are a schematic of a chemical procedure for synthesizing a disulfide cross-linked hydrogel, a type of chemical-responsive hydrogel. Various molar ratios of AAm and NAPMAAm monomers are diluted in water (FIG. 6A). Free radical polymerization of monomers form co-polymer chains with reactive primary amine groups (FIG. 6B). Reaction with N-Succinimidyl-S-acetylthiopropionate (SATP) (FIG. 6C) and deprotection with hydroxylamine (FIG. 6D) yields sulfhydryl functional copolymer chains in solution (FIG. 6E). Formation of disulfide bonds results in cross-linked hydrogel (S—S-coPAAm) (FIG. 6F).

FIG. 7 shows pictures of bulk S—S-coPAAm hydrogels with varying mol % NAPMAAm and their subsequent dissolution upon exposure to varying amounts of TCEP with mixing. A more rigid hydrogel structure can be observed for higher cross-linking density (higher mol % NAPMAAm). Also, more TCEP is needed to completely dissolve hydrogels with higher cross-linking density, as would be predicted by theory.

FIGS. 8A-C relate to optical characterization of hydrogel and its infiltration into a PSi sensor template. FIG. 8A is a graph of the refractive indices of bulk S—S-coPAAm hydrogels with varying mol % NAPMAAm measured on a bench-top Abbe refractometer. The negative control (0 mol % NAPMAAm) did not form hydrogel, but the bulk refractive index of the polymer solution was measured. FIG. 8B shows the raw reflectance spectra measured using an Avantes spectrometer, illustrating wavelength shifts associated with the addition of mercaptosilane (MPTS), filling of the PSi pores with water, and the swollen S—S-coPAAm hydrogel after 2 day soak in water. FIG. 8C is a graph of the optical wavelength shift response of PSi sensors when S—S-coPAAm hydrogels with varying mol % NAPMAAm fill the pore volume, comparing the results experimentally determined with simulation results.

FIG. 9A shows side views of 10 mol % NAPMAAm S—S-coPAAm hydrogels (bulk or cross-linked into a PSi sensor) before and after exposure to 1 ml of 50 mM TCEP for 15 minutes, rinsing with water, and air drying for 5 minutes. FIG. 9B is a series of photographs (top down views) of 4.14 mol % NAPMAAm S—S-coPAAm hydrogels cross-linked into PSi Bragg mirrors after incubation in 1 ml of varying concentrations of TCEP solution on a shaker for 15 minutes, subsequent rinsing with water, and air-drying for 5 minutes. Color shift from red to green is evident.

FIG. 11 is a schematic drawing depicting the formation of hydrogels made using polyacrylamide/N-(3-aminopropyl)-methacrylamide random copolymers.

FIG. 12 is an illustration of Morphine-3-glucuronide (M3G).

FIGS. 13A-D are photographs showing the formation of target responsive gels synthesized by incorporation of M3G (target analog) on the polymer chain backbone and addition of anti-morphine Ab and Protein G to form cross links. Trypan blue was added to aid in the visualization of the gel. Gels withstood cycles of dehydration and rehydration. Addition of free M3G caused gel dissociation after 15 minutes. Similar results have been achieved with morphine in place of M3G.

FIGS. 15A-C demonstrate that spin coating can be used to cast gel precursor solution on a PSi sensor. FIG. 15A is an SEM image of thick gel on a PSi sensor (scale bar 2 µm). FIG. 15B is a graph of gel thickness spin coated on a silicon wafer as a function of spin speed. FIG. 15C is a graph of the wavelength shift as a function of spin speed for gel precursor spin coated onto PSi sensors. After gel formation the optical wavelength shift measured equaled expectations, validating complete pore infiltration.

DETAILED DESCRIPTION OF THE INVENTION

The present invention relates to products that include an optical sensor, a polymer matrix on a surface of the optical sensor, and one or more high refractive index nanoparticles within the polymer matrix. In use, the optical sensor can be used to detect changes in a refractive index of the polymer matrix in the presence of a target molecule. As discussed more fully below, the high refractive index nanoparticles have the effect of enhancing the refractive index change that is detected, thereby rendering the optical sensor much more sensitive to subtle changes in the polymer matrix caused by presence of the target, even allowing a signal change detectable by the naked eye.

Figure 1A:
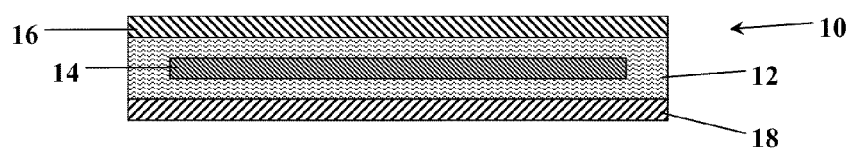
FIGS. 1A-C are schematic illustrations of a representative TRAP-gel-PSi sensor (FIGS. 1A-1B), and a magnified sensor showing cross-link dissociation, gel swelling, and eventual out diffusion in the presence of target (FIG. 1C).

Referring to FIG. 1A, one embodiment of the product 10 is shown to include a polymer matrix 12 with an optical sensor 14 fully embedded in the polymer matrix. On one side of the polymer matrix is a vapor barrier 16. The vapor barrier can be retained on the polymer matrix using either a mechanical connection of the matrix to the barrier or a chemical bonding. On an opposite side of the polymer matrix is a release layer 18. The release layer 18 is intended to be removed from the polymer matrix during use, allowing the polymer matrix to be exposed for combining with a sample to be screened. In this embodiment, the matrix covers all exposed surfaces of the optical sensor.

Figure 1B:
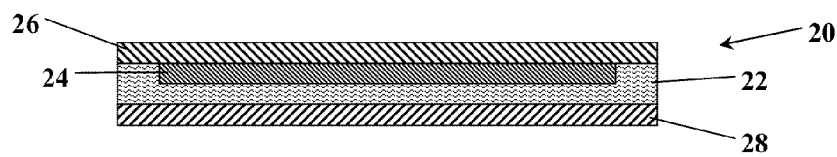
Figure 1C:
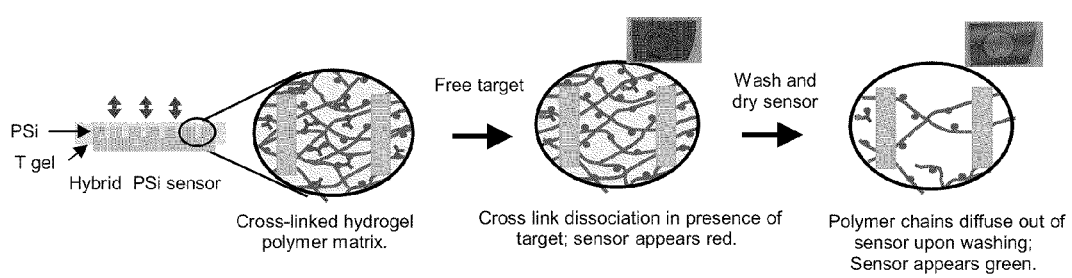

Referring to FIG. 1B, another embodiment of the product 20 is shown to include a polymer matrix 22 with an optical sensor 14 partially embedded in the polymer matrix. On one side of the polymer matrix (and optical sensor) is a vapor barrier 16. The vapor barrier can be retained on the polymer matrix as described above. On an opposite side of the polymer matrix is a release layer 18. The release layer 18 is intended to be removed from the polymer matrix during use, allowing the polymer matrix to be exposed for combining with a sample to be screened. In this embodiment, the matrix covers only a portion of the surfaces of the optical sensor.

The optical sensor can have any suitable design or construction that is compatible for the target molecule detection in the matrix environment. Exemplary optical sensor constructions include, without limitation, single layer materials, double layer architectures, mirrors, microcavities, rugate filters, and stacked combinations of these features. These include simple porous structures of the type disclosed in U.S. Pat. No. 6,248,539 to Ghadiri et al., which is hereby incorporated by reference in its entirety, as well as microcavity structures of the type disclosed in Vinegoni et al., "Porous Silicon Microcavities," in 2 SILICON-BASED MATERIALS AND DEVICES 122-88 (Hari Nalwa ed., 2001); U.S. Patent Application Publ. No. 2006/0276047 to Ouyang et al.; U.S. Pat. No. 7,226,733 to Chan et al.; and DeLouise & Miller, *Proc. SPIE* 5357:111 (2004), each of which is hereby incorporated by reference in its entirety.

These sensor constructions utilize porous materials, which in the present invention facilitates matrix infiltration of the pores. The pores (or cavities) in the porous sensor are typically sized in terms of their nominal "diameter" notwithstanding the fact that they are somewhat irregular in shape and may vary in diameter. Pore diameters ranging from about 2 nm to about 10 μm are particularly desired, with diameters of about 10 to about 100 nm being preferred for visible light, about 2 to about 50 nm diameters being preferred for ultraviolet light, and 100 to 2000 nm being preferred for infrared light. Thus, in certain embodiments the sensor construction may be characterized generally as mesoporous: having pores between about 2 to about 50 nm), nanoporous (having pores less than about 2 nm), or macroporous (having pores greater than about 50 nm). The nominal pore diameter should also be selected based upon the size of the target molecule(s) to be detected, and the dimensions of the high refractive index nanoparticles.

The porous materials used to fabricate the sensor constructions are preferably semiconductor materials. Semiconductor substrates which can be used to form the sensor can be composed of a single semiconductor material, a combination of semiconductor materials which are unmixed, or a mixture of semiconductor materials.

Semiconductor substrates which can be used to form the porous semiconductor material according to the present invention include, without limitation, silicon and silicon alloys. The semiconductor substrate is amenable to galvanic etching processes, which can be used to form the pores. These semiconductor materials can include, for example, group IV materials, including intrinsic or undoped silicon, p-doped (e.g., $(CH_3)_2Zn$, $(C_2Hs)_2Zn$, $(C_2H_5)_2Be$, $(CH_3)_2Cd$, $(C_2H_2)_2Mg$, B, Al, Ga, In) silicon, n-doped (e.g., $H_2Se$, $H_2S$, $CH_3Sn$, $(C_2H_5)_3S$, $SiH_4$, $Si_2H_6$, P, As, Sb) silicon, intrinsic or undoped germanium, and doped germanium; mixtures of these materials; semiconductor materials based on Group II materials; semiconductor materials based on Group III-V materials (e.g., AN, GaN, InN, $In_xGa$, $In_xAs$, $Al_xGai_xAs$, GaAs, InP, InAs, InSb, GaP, GaSb, Al oxides, and combinations thereof); and semiconductor materials based on Group VI materials.

The porous semiconductor materials can be fabricated according to any known procedures, e.g., those disclosed in Vinegoni et al., "Porous Silicon Microcavities," in 2 SILICON-BASED MATERIALS AND DEVICES 122-88 (Hari Nalwa ed., 2001); U.S. Patent Application Publ. No. 2006/0276047 to Ouyang et al.; U.S. Pat. No. 7,226,733 to Chan et al.; DeLouise & Miller, Proc. SPIE 5357:111 (2004); and U.S. Patent Application Publ. No. 2007/0007241 to DeLouise et al., each of which is hereby incorporated by reference in its entirety. Basically, single layer devices can be fabricated by applying a constant current for a fixed period of time to achieve a substantially uniform porosity. Multilayer devices can be fabricated by cycling between different current densities for desired time periods to produce different porosity layers. The electrochemical fabrication process can be controlled to produce a wide range of pore diameters and pore channel morphologies (dendritic to highly anisotropic).

Single and multilayer porous semiconductor structures are useful for substance delivery, and multilayer devices are particularly useful for optical sensing applications. The optical properties of the layer(s) may be designed for regulating the time release characteristics of the porous semiconductor material.

The optical sensor can be any suitable thickness depending upon the intended use, but preferably less than about 25 microns, more preferably between about 2 to about 15 microns. Typically, the thickness will vary inversely according to the desired porosity (i.e., higher porosity structures will be thicker than lower porosity structures) as well as according to the wavelength of light to be detected (i.e., structures which are used with shorter wavelength light can be thinner than structures which are used with longer wavelength light).

The optical sensor can optionally be removed from its underlying solid substrate using an electropolishing step (see U.S. Patent Application Publ. No. 2007/0184222 to DeLouise and Miller, which is hereby incorporated by reference in its entirety) prior to embedding in the matrix. As a consequence, the porous semiconductor material that forms the optical sensor can made flexible, allowing the product to be applied to a curved surface.

Alternatively, the optical sensor can be formed on a solid support (e.g., on a silicon wafer substrate or a glass substrate). In at least one embodiment, the solid support forms a vapor barrier described above.

In at least on embodiment, the porous semiconductor material is a microactivity biosensor of the type disclosed in U.S. Pat. No. 7,226,733 to Chan et al., which is hereby incorporated by reference in its entirety.

The polymer matrix includes strands of one or more polymers (or co-polymers) that are reversibly cross-linked together by a cross-linking agent. As discussed more fully below, the cross-linking agent has an affinity for the target molecule, whereby the presence of target will break cross-links causing the matrix to swell. While swelling will produce a corresponding η change that can be optically detected with a reader, in preferred embodiments the majority of cross-links will dissociate and polymer chains will wash out of the sensor in the presence of a threshold concentration of the target molecule, thereby producing a visible color change that can be viewed by the naked eye when the sensor is dried. The polymer matrix may also optionally include one or more permanent cross-links (i.e., not broken in the presence of target). Permanent cross-links may be formed using suitable methods, which will be apparent to the skilled artisan.

The polymer used to form the matrix can be any suitable polymer material. Matrix polymers, effective in this invention include but are not limited to: Nylons, including without limitation Nylon 6,6 and Nylon 6,10; polyurethanes, polyacrylonitrile, polyvinyl alcohol, polylactic acid, polyethylene-co-vinyl acetate, polycarbonate, poly(iminocarbonate)s, polymethacrylates, poly(alkyl methacrylic acid)s, polyacrylates, poly(alkyl acrylic acid)s, poly(N,N'-diethylaminoethyl methacrylate), poly(N,N'-dialkylaminoalkyl acrylamides), poly(ethylene oxide)/PEO, polyethylene amines, polyethylene terephthalate, polystyrene, polyvinyl chloride, poly vinyl phenol, polyacrylamide, poly(N-alkyl acrylamide)s, polyglycolic acids, poly lactic-co-glycolic acids, polycaprolactone, poly(-hydroxyethyl methacrylate) (polyHEMA), poly(vinylidene fluoride), poly(vinylidene chloride), poly(ethylene glycol)/PEG, polyvinyl pyrrolidone, polyethylene, polypropylene, poly(-hydroxybutyrate), poly(ortho esters), polyanhydrides, poly(ether-ester) azopolymers, poly(dimethyl siloxane), poly(phosphazene)s, other copolymers of the above homopolymers (e.g., poly(methacrylic acid-co-ethylene glycol), and others.

Matrix polymers may also comprise natural polymers, such as agarose, collagen, keratin, silk, silk-like protein polymers, elastin, elastin-like protein polymers, poly(amino acids), cellulose acetate, hyaluronic acid, chitosan, fibronectin, and others.

Combination fibers comprising mixtures of different synthetic and/or natural polymers can also be prepared. Polymer combinations help to optimize solubility and mechanical properties of the fibers.

In one embodiment, the polymer matrix comprises a hydrogel polymer, comprising synthetic hydrogels, natural hydrogels, and mixtures thereof. A hydrogel matrix is particularly well suited for the present invention, because the properties of the hydrogel material can be tailored to maintain environmental conditions (e.g., hydration, pH, and ionic strength) while enabling binding and recognition to occur in a more "solution-like" environment.

Any of a variety of known hydrogels can be adapted for use in the products of the present invention. Exemplary hydrogels include, without limitation, those found in commercial or investigative products available from Johnson & Johnson (e.g., NU-GEL® Wound Dressing, NU-GEL® Collagen Wound Gel), Coloplast, 3M (e.g. 3M™ Tegaderm™ Absorbent Clear Acrylic Dressing), and prototype composites supplied by ConMed (e.g., ClearSite® TM Transparent Membrane), as well as hydrogels formed using any of the above-identified natural or synthetic polymers and those disclosed in Peppas et al., *Biomed. Engin.* 2:9-29 (2000); U.S. Pat. No. 6,855,743 to Gvozdic (polyvinyl alcohol hydrogels); U.S. Pat. No. 6,800,278 to Perrault et al. (e.g., acrylated quaternary ammonium monomelic hydrogels); U.S. Pat. No. 6,861,067 to McGhee et al. (polyurethane hydrogels); U.S. Pat. No. 6,710,104 to Haraguchi (organic/inorganic hybrid hydrogels); U.S. Pat. No. 6,468,383 to Kundel (e.g., hydrogel laminates formed by crosslinking of one or more hydrophilic polymers); U.S. Pat. No. 6,238,691 to Huang (polyurethane hydrogels with, optionally, antimicrobial and/or bacteriostatic agents); and U.S. Pat. No. 5,932,552 to Blanchard et al. (hydrogels formed of cross-linked keratin), each of which is hereby incorporated by reference in its entirety. As will be apparent to one of skill in the art, the hydrogels may also include additional agents useful for the application of choice including, for example, antimicrobial agents, bacteriostatic agents, antiviral agents, and antifungal agents.

In the present invention, the polymer matrices preferably include a side group (e.g., amines, carboxylic acids, thiols) that is suitable for tethering a reagent useful for polymer cross-linking By way of example, amine-containing polyacrylamide (NAPMAAm/AAm) chains can be prepared by radical copolymerization of acrylamide (AAm, Sigma) with aminopropyl-methacrylamide (NAPMAAm, Polysciences) monomers using sodium formate (HCOONa, Sigma) to control chain length. Using known synthesis schemes (Bonanno & DeLouise, *Proc. SPIE* 7167:11 (2009), which is hereby incorporated by reference in its entirety), it is possible to synthesize copolymer chains that vary in molecular weight ($M_w$ 10-100 kDa) and the number of amine reactive sites per chain (2-20 mol %). In this embodiment, polymer chains with $M_w$<150 kDa are utilized to afford a sufficiently porous gel environment.

The cross-linking agent can be any suitable agent capable of reversibly binding to one or more of the polymer strands with the matrix. In one embodiment, the cross-linking agent is formed using one or more receptors and one or more target analogs. The receptors reversibly bind to the target analogs, albeit with a lower affinity than the target molecule. Thus, in the presence of the target molecule, the target analog is displaced, breaking the cross-link between polymer strands. Breaking the reversible cross-links results in swelling of the polymer matrix and a change in the refractive index of the polymer matrix.

In one embodiment, the one or more high refractive index nanoparticles are nonspecifically encapsulated in the polymer matrix. In this embodiment, swelling of the polymer matrix in the presence of the target results in release of at least one of the nanoparticles from the polymer matrix, whereby a change in the refractive index of the polymer matrix occurs. In other embodiments, the one or more high refractive index nanoparticles are specifically retained in the polymer matrix (via one of the cross-linking reagents and/or via direct attachment to the polymer matrix). Alternatively, both non-specific and specific retention of the nanoparticles can be utilized. Combining non-specific and specific nanoparticle retention in the same optical sensor may be useful for tuning the magnitude of the amplification that occurs at different target concentrations.

In certain embodiments, one or more receptors and/or one or more target analogs are also coupled to the one or more nanoparticles. In this embodiment, the one or more receptors, the one or more target analogs, and the one or more nanoparticles collectively form one or more reversible crosslinks within the polymer matrix. Binding of one of the target molecules to one of the receptors results in displacement and release of at least one of the nanoparticles from the polymer matrix, whereby a change in the refractive index of the matrix occurs.

In a further embodiment, one or more receptors or one or more target analogs are coupled to the polymer matrix and the other of the one or more receptors and the one or more target analogs is coupled to the one or more nanoparticles, whereby the one or more nanoparticles are reversibly bound to the polymer matrix. Binding of one of the target molecules to one of the receptors results in displacement and release of at least one of the nanoparticles from the polymer matrix, whereby a change in the refractive index of the matrix occurs.

In these various embodiments, the one or more receptors can be monovalent, i.e., capable of binding only a single target analog or target at a time. Alternatively, the one or more receptors can be multivalent, i.e., capable of binding to more than one target analog or target at a time.

The one or more receptors can be any molecule that can be used to form a labile bond. Exemplary classes of receptor molecules include, without limitation, non-polymeric small chemical molecule complexes (e.g., BIS (which forms non-reversible crosslinks), BAC (which forms reversible crosslinks)), peptides, polypeptides, proteins, peptide-mimetic compounds, antibody complexes (e.g., whole antibodies, antibody fragments, recombinant single chain variable fragment antibodies (scFv)), oligonucleotides (e.g., nucleic acid molecules, sDNA, RNA), nucleic acid aptamers, enzymes, and ribozymes. Specific sub-classes include receptors for cell surface molecules, lipid A receptors, antibodies or fragments thereof, peptide monobodies, lipopolysaccharide-binding polypeptides, peptidoglycan-binding polypeptides, carbohydrate-binding polypeptides, phosphate-binding polypeptides, nucleic acid-binding polypeptides, polypeptides that bind an organic warfare agent, and polypeptides that bind to specific protein or polypeptide targets.

The target analogs can be any agent that structurally and/or functionally mimics the target, but has a lower affinity for the receptor than the target. Thus, target analogs can be derivatives of the target. In some instances, specific attachment of a target molecule to a polymer chain and/or cross-linking agent alters a the receptor's binding affinity for the target molecule. In such cases, the target molecule itself may be used as the target analog, provided the receptor has a lower binding affinity for the specifically-attached target molecule than for unbound target.

Target molecules that can be detected in accordance with the present invention include, without limitation, antigens, antibodies, proteins, glycoproteins, peptidoglycans, carbohydrates, lipoproteins, lipoteichoic acid, lipid A, phosphates, nucleic acids, pathogens, host markers of infection, organic warfare agents, organic compounds, drugs of abuse, opiates, pain killers, explosives, biomolecules (e.g., metabolites), antimicrobial peptides, immune function markers, cancer markers, and disease markers.

In one embodiment, the detectable change in refractive index occurs at a target molecule concentration of between picograms per milliliter and milligrams per milliliter. In another embodiment, the detectable change in refractive index occurs at a target molecule concentration in the nanomolar to micromolar range.

Exemplary target molecule/target analogs include, without limitation, a first oligonucleotide and a second oligonucleotide that contains one or more mismatches with respect to a receptor oligonucleotide; drug compounds (including aptamers for recreational drug molecules (see U.S. Patent Application Publ. No. 2003/0224435 to Seiwert, which is hereby incorporated by reference in its entirety) such as morphine and structural analogs of morphine such as morphine-3-glucuronide (M3G), which has a lower affinity for certain morphine binding antibodies; avidin or streptavidin/antibodies that bind to biotin with lower affinity that either avidin or streptavidin; antibodies for detection of environmental pollutants (polychlorinated biphenyls, polyaromatic hydrocarbons), neurotransmitters (acetylcholine), peptide hormones, microbial pathogens, etc.

Figure 2:
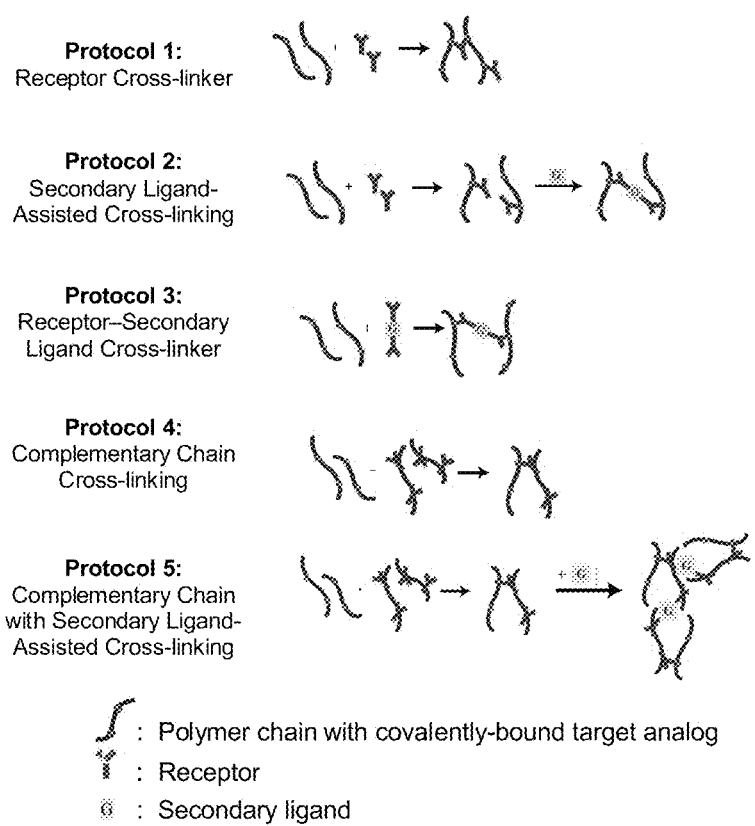
FIG. 2 is a schematic illustration of exemplary protocols for cross-link formation.

One exemplary system, illustrated in FIG. 2 (Protocol 1), includes polymer strands that can be covalently linked with a target analog, and then cross linked with a receptor specific for the target analog. Receptor cross-links specific for the target analog can be displaced in the presence of target, because the receptor has greater affinity to the target than to the target analog.

Another exemplary system, illustrated in FIG. 2 (Protocol 2), includes polymer strands that can be covalently linked with a target analog, and then cross linked with a pair of receptors specific for the target analog along with a secondary ligand (e.g., Protein G (two antibody binding sites) or Protein A (four antibody binding sites)). This effectively spaces the polymer chains further apart and promotes greater porosity to the polymer. As with the Protocol 1 system, receptor cross-links specific for the target analog can be displaced in the presence of target.

A related system, illustrated in FIG. 2 (Protocol 3), includes polymer strands that can be covalently linked with a target analog, and then cross linked with a pre-assembled linker that includes two or more receptors specific for the target analog along with a secondary ligand (e.g., Protein G (two antibody binding sites) or Protein A (four antibody binding sites)). As with the Protocol 1 and 2 systems, receptor cross-links specific for the target analog can be displaced in the presence of the target.

Yet another system, illustrated in FIG. 2 (Protocol 4), includes two sets of polymer strands for co-polymer matrix formation. One set of strands is functionalized for covalent bond formation with a target analog, and a second set of strands is functionalized with a receptor specific for the target analog. Cross-linking of the strands is directly between the two agents (receptor and target analog). Receptor-target analog cross-links can be displaced in the presence of target.

A related system, illustrated in FIG. 2 (Protocol 5), also includes two sets of polymer strands for co-polymer matrix formation. As with Protocol 4, one set of strands is functionalized for covalent bond formation with a target analog, and a second set of strands is functionalized with a receptor specific for the target analog. In this embodiment, both direct cross-linking as in Protocol 4 and secondary ligand (e.g., Protein G/A)-assisted cross-linking is utilized. Receptor cross-links specific for the target analog can be displaced in the presence of target.

The protocols illustrated in FIG. 2 can be modified to detect any target of interest using suitable target-specific receptors and target analogs as described herein. The one or more high refractive index nanoparticles can be incorporated into the polymer matrix in each of the exemplary protocols in a variety of ways, including: (a) specific attachment to one or more of the polymer chains, (b) specific attachment to one or more of the receptors, (c) specific attachment to one or more of the target analogs, (d) specific attachment to the secondary ligand, (e) nonspecific encapsulation, and (f) combinations of (a)-(e). Specific attachment in (a)-(d) may be carried out by any number of methods, including covalent attachment to the respective agent and/or indirect attachment via, e.g., a second receptor-ligand interaction in which the second receptor is specific for the high refractive index nanoparticle (for example, the nanoparticle or the agent to which it is specifically attached is functionalized with biotin and the other is functionalized with streptavidin). Regardless of the mode for introducing the high refractive index nanoparticles into the matrix, the nanoparticles are preferably loaded into the gel at about 0.01 to about 50 wt %, more preferably about 0.1 to about 10 wt %.

The one or more high refractive index nanoparticles can be formed of any suitable material. In one embodiment, the refractive index of the nanoparticles is greater than 1.5. In another embodiment, the refractive index of the nanoparticles is at least 1.7. In another embodiment, the refractive index of the nanoparticles is greater than 2.0. In another embodiment, the refractive index of the nanoparticles is at least 2.5. In a further embodiment, the refractive index of the nanoparticles is at least 3.6.

The nanoparticles can be any size between about 1 nm and about 1000 nm, preferably between about 2 nm and about 750 nm. In preferred embodiments, the nanoparticles have a diameter that is small enough to diffuse out of the pores of the optical sensor. By way of example, the nanoparticles are preferably between about 5 and about 100 nm, more preferably between about 5 and about 50 nm.

Exemplary high refractive index nanoparticles include, without limitation, InP, PbS, PbSe, CdSe, ZnS, CdSe core ZnS shell, CdTe, CdS, Si, FexOy, $TiO_2$, $AlxOy$, ZnOs, SiC, TiC, and other oxides and carbides and core/shell types.

Coating of the optical sensor surface with a well-controlled polymer thickness can be carried out by spin coating the optical sensor with a polymer solution. Inducing cross-link formation can be performed before, during, or after spin-coating. Preferably, in the final product, any polymer matrix remaining on an exterior surface of the porous matrix is less than 50 microns thick, more preferably less than about 100 nanometers thick. In a preferred embodiment, the pores of the porous matrix are substantially filled with the polymer matrix, while the exterior surface of the product is substantially free of the polymer matrix.

The product, once formed, is intended to be used with a sample to be tested. The sample can be actively introduced to the polymer matrix. In certain embodiments, the product can be applied at a wound site or on uninterrupted skin or tissue so that the sample is passively absorbed into the polymer matrix. Regardless, the fabrication procedures are intended to be conducted in a sterile environment so as to prevent contamination. Moreover, the sterile product, once prepared, is intended to be packaged in a sterile packaging to allow for distribution and handling prior to end use. Sterile packaging procedures are known in the art.

Another aspect of the present invention is a method of making a product of the invention. This method involves preparing an optical sensor and at least partially embedding the optical sensor in a hydrogel matrix.

Typically, one or more polymer solutions is poured or spin coated onto the optical sensor, thereby infiltrating the pores, and cross-linking is allowed to take place. Because cross-linking generally takes several days, suitable cross-linking agents may be added to the polymer solution(s) before, during, or after the one or more polymer solutions are poured or spin-coated onto the matrix, provided cross-linking primarily takes place within the optical sensor. The cross-linking can be carried out as described above. The high refractive index nanoparticles may likewise be added before, during, or after the one or more polymer solutions are poured or spin-coated onto the optical sensor. In at least one embodiment, one or more high refractive index nanoparticles are encapsulated within the polymer matrix by: dissolving the polymer precursor(s) into a solution containing the high refractive index nanoparticles, adding the cross-linking agents, and then pouring or spin-coating the resulting polymer solution over the optical sensor. In at least another embodiment, the high refractive index nanoparticles are covalently bound to one or more cross-linking agents before being added to the polymer solution(s). In at least another embodiment, the high refractive index nanoparticles are covalently bound to one or more polymers before the polymer solution(s) are poured or spin-coated onto the optical sensor. Combinations of the three preceding embodiments are also contemplated.

Although in certain embodiments the products are intended to be used with ambient light or a direct light source to produce a change in refractive index that is detectable by eye (e.g., from red to green), in other embodiments changes in the refractive index that are too subtle to be measured by eye can be measured using a detection device that includes, in addition to the product, a source of illumination and a detector positioned to capture light reflected from the product and to detect changes in the refractive index of the hydrogel matrix. Exemplary detectors include, without limitation, collecting lenses, monochrometers, and spectrometers. A computer with an appropriate microprocessor can be coupled to the detector to receive data from the device and analyze the data to compare the optical response (reflected light, transmitted light, and/or photoluminescence) before and after exposure of the device to a target molecule. Many widely available detectors afford the detection of optical shifts of about 0.001 nm or greater.

A further aspect of the present invention relates to a method of detecting a target molecule in a sample. Basically, a product of the present invention is exposed to a sample under conditions effective to allow binding of a target molecule in the sample to the one or more receptors, thereby displacing the target analogs. After such exposure, it is determined whether the biological sensor emits an optical response (reflected light, transmitted light, and/or photoluminescence) emission pattern which has shifted due to the change in refractive index. If a detectable change is not detected, then the target molecule is not present in the sample (or is present below the limit of detection). However, if a detectable change is detected, then the target molecule is present in the sample.

To determine whether a shift has occurred, a first (baseline) optical response (reflected light, transmitted light, and/or photoluminescence) emission pattern is measured prior to exposure to a sample. After exposure to the sample, a second optical response emission pattern is measured and the first and second emission patterns are compared. A shift as little as about 0.001 nm can indicate the presence of the target in the sample. However, to facilitate large shifts that are more easily detected, following exposure any swelled polymer matrix and high refractive index nanoparticles can be washed from the optical detector. After washing, the second measurement can be made. For detection by naked eye, the baseline measurement can be simply noting the color of the optical sensor before sample exposure.

As noted above, the optical sensor (and product containing the same) can be used to detect the presence of a target (e.g., pathogen) in a sample. Samples which can be examined include blood, water, urine, sweat, a suspension of solids (e.g., food particles, soil particles, etc.) in an aqueous solution, or a cell suspension from a clinical isolate (such as a tissue homogenate from a mammalian patient). For example, the product may be used to detect a pathogen in a sample. Other exemplary uses include, without limitation, pregnancy tests and diabetes test strips.

As will be apparent to one of ordinary skill the art, one or more therapeutic agents may optionally be retained within the polymer matrix as described in U.S. Patent Application Publ. No. 2007/0184222 to DeLouise and Miller, which is hereby incorporated by reference in its entirety, such that the therapeutic agents are released from the product when the cross-links break in the presence of the target. In such embodiments, the amplified change in refractive index can serve as an optical (e.g., visual) confirmation of therapeutic agent delivery. The cross-link architecture can be designed to release varying concentrations of the therapeutic agent at varying target concentrations.

Yet another aspect of the present invention is a method of detecting a pathogen and/or infection at a wound site. This method involves providing a product according to the present invention in which the polymer matrix contains one or more cross-linking agents specific for a target molecule (of the pathogen or host marker of infection to be detected). In the presence of the target molecule, the polymer matrix will destabilize and swell, allowing the high refractive index nanoparticles and polymer matrix to wash away from the optical sensor. As a result, the refractive index of optical sensor changes, causing a detectable shift in the optical properties of the optical sensor. Detection of the pathogen/infection can be made without removing the optical sensor/product from the wound site, in which case a light source and spectrometer may need to be used to detect any change in the refractive index. Alternatively, detection of the pathogen/infection can be made following removal of the optical sensor/product from the wound site, and after washing any swollen or destabilized polymer and high refractive index nanoparticles from the optical sensor surface.

EXAMPLES

The following examples are provided to illustrate embodiments of the present invention but are by no means intended to limit its scope.

Example 1

PSi Transducer Substrate Preparation and Characterization

The methods employed to produce the macroporous silicon sensors used in Examples 1-6 have been described in detail elsewhere (Kilian et al., *ACS Nano* 1(4):355-61 (2007); DeLouise & Miller, *Anal. Chem.* 77(10):3222-30 (2005), each of which is hereby incorporated by reference in its entirety). Briefly, PSi mirror structures were fabricated from n+ <100> silicon wafers (Sb doped, 0.01-0.08 Ω-cm) using a room temperature electrochemical etch process. The aqueous electrolyte contained BASF Pluronic L31 (0.1%) surfactant and hydrofluoric acid (5% HF). The mirror structure used in Examples 1-6 was fabricated with alternating current densities of 40 and 70 mA/cm$^2$ to yield 16 alternating layers of 71 and 84% porosity with a total thickness of ~2.9 μm measured by SEM. The PSi samples were thermally oxidized in dry $O_2$ at 900° C. to enhance stability of the PSi and to create hydrophilic pore channels. These devices exhibit a wavelength shift sensitivity (WSS) of the 205 nm/RIU determined by infiltrating liquids with varying η into the porous matrix and measuring the magnitude of the wavelength shift. WSS is the slope of a plot of wavelength shift vs. η.

Example 2

Preparation Glutathione Coated Quantum Dots

Commercial CdSe/ZnS core/shell octadecylamine (ODA)-capped Quantum Dots™ (QDs) (620 nm emission, NN-Labs, #CZ620) in toluene were used in Examples 3-4. Glutathione-capped QDs (GSH-QDs) were synthesized in-house via a ligand exchange procedure. Efficient ligand exchange requires working with solvent systems in which ligands are readily soluble. It was observed that ODA ligand exchange does not work efficiently in toluene. Therefore, QDs were first transferred to tetrahydrofuran (THF). A 200 μl aliquot of stock QDs was added to a methanol:acetone (1:1) solution and separated by centrifugation at 14,000 rpm for 5 minutes. Toluene was decanted and QDs were resuspended in 200 μl of tetrahydrofuran (THF).

GSH was added to methanol and the pH of the solution adjusted to pH=11 with tetramethylammonium hydroxide pentahydrate $((CH_3)_4NOH.5H_2O)$. The GSH methanol solution (20 mg/mL, 1 mL) was slowly added to the THF QD solution (0.25 μM, 200 μL) of CdSe/ZnS QDs at room temperature. The mixture was stirred at 60° C. for 2 hours and precipitated with the addition of ether by centrifugation at 14,000 rmp for 5 minutes. The supernatant was discarded and the QD sample was redispersed in deionized water. The solution was filtered through a 300 KDa membrane filter (Microsep Centrifugal Filter, Pall Life Sciences) for purification. Excess GSH was removed by the dialysis against deionized water using Micro DispoDialyzer 5000 MWCO (Harvard Apparatus). Surface charge (zeta potential) and hydrodynamic radius were measured using Malvern Instruments Nanosizer. Results are reported in Table 1 below.

TABLE 1

Optical Properties of QD Nanoparticles.

| Sample | Quantum yield (%) | Zeta potential (mV) | Hydrodynamic diameter (nm) |
|---|---|---|---|
| ODA-QDs | 56 | N/A | N/A |
| GSH-QDs | 40.7 | −23.8 | 20.9 |

Example 3

Preparation of Hydrogel-PSi Hybrid Sensors

For Examples 3-4, an acrylamide (AAm) polymer crosslinked with N,N'-methylenebisacrylamide (BIS) and N,N Bis-acryloyl cystamine (BAC) formulated with a molar ratio of 195:4:1 Aam:BAC:BIS was used. The measured polymer density is 1.020 g/ml. BAC contains a disulfide linkage that cleaves under suitable reducing conditions to cause swelling of the polyacrylamide (PA) gel. In this Example, 50 mM Tris[2-carboxyethyl]phosphine (TCEP) reducing agent was used. All monomers (AAm, BAC, Bis) were diluted in an aqueous 25 v/v % ethanol stock solution. The monomer stock solution contained 0.05 g AAm, 0.00376 g BAC, 0.000556 g Bis, 135.78 µL ethanol, and 407.35 µL water, to yield a 10 wt % monomer stock solution. N,N,N'N'-(Tetramethylethylenediamine) (TEMED) was added to the monomer stock solution at 2.1 wt % (1.46 µL). To prepare hybrid PSi devices, 15 µL of monomer stock solution was added to either 15 µL of water for control or 15 µL of a 17.8 µM GSH-QD solution prepared as described in Example 2 to yield a final 5 wt % hydrogel. The QD loading was estimated to be 0.29 wt %. The gel/QD solution was ultrasonicated for 1 minute. Ammonium persulfate (APS) initiator (2 µL of 2 wt %) was used as a free radical generator to initiate polymerization. APS (2 µL) was added to the monomer solutions and mixed quickly with a pipette. Within ~30 seconds, ~10 µL of the solutions were pipetted into a custom glass fixture that restricts oxygen presence and controls thickness of the gel height above the PSi sensor to be the thickness of teflon tape (~100 µM). The remaining polymer with APS initiator (~20 µL) was left in the eppendorf tube and kept closed to restrict oxygen to create bulk hydrogels for $\eta$ measurements made using a bench-top Abbe refractometer (Bausch & Lomb). All gels were left for overnight to cross-link at room temperature in the dark.

Example 4

Optical Detection with Hybrid-PSi Sensors

The optical reflectance spectra were measured using an Advantes 3648-USB2 spectrophotometer with an optical resolution of 0.06 nm pixel$^{-1}$. An incident beam of white light (spot size ~1.3 mm$^2$) was illuminated at normal incidence. All plots containing error bars represent the standard deviation of each data point taken with a minimum of n=2 for interday experiment trials and 3 measurement locations per sensor. Reflectivity spectra were first recorded following thermal oxidization of the PSi sensors. Next, the wavelength shift for water filling pores was measured as a reference for each location on chip. Chips were dried with N$_2$ gas and the hydrogel was cast into the sensor as explained in Example 3. The cross-linked gels were soaked overnight in 5 mL water at room temperature to allow for equilibrium swelling and possible QD out-diffusion. The hybrid-PSi sensors were then held within a custom fixture under 10 mL of PBS and the wavelength shifts were measured in 3 identical locations. Finally, 500 µL of 50 mM TCEP reducing agent was added to hybrid sensor/gels and temporal blue wavelength shift response was monitored for 2 hours at a single location. The hybrid-PSi sensors were then rinsed with DI water 3 times to remove TCEP ($\eta$=1.3368) from the sensor and resulting wavelength shifts remeasured in 3 identical locations. The magnitude of wavelength shifts reported are in reference to water filling the pores.

Figure 3:
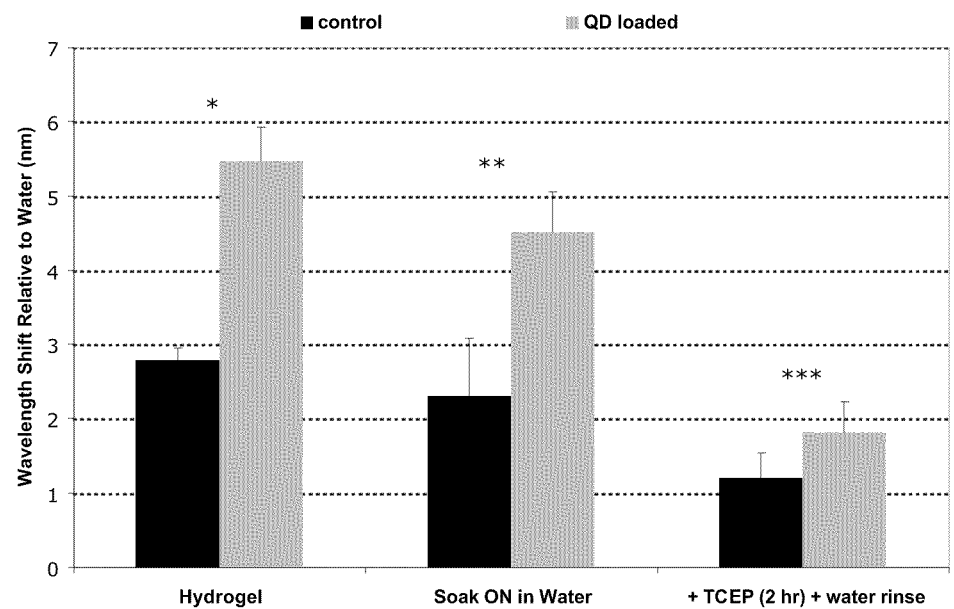
FIG. 3 is a graph of the relative wavelength shift (nm) for processing of hybrid optical sensor constructs illustrating the optical signal enhancement afforded by incorporation of 0.29 wt % high refractive index Quantum Dot™ nanoparticles in a 5 wt % polyacrylamide hydrogel. ON=overnight; TCEP=Tris [2-carboxyethyl]phosphine.

Optical shifts for casting the control and QD (~8.9 µM, 0.29 wt %) loaded hydrogels into the PSi sensor matrix and following over night (O/N) water soak and exposure to TCEP reducing agent (2 hours) are listed in Table 2 and displayed in FIG. 3. The wavelengths shifts recorded immediately after casting the hydrogel and following O/N soak water are in reference to pure water filling the pores. Results show the sensor hybrid containing the gel loaded with the high refractive index QD produced a statically significant 2× larger shift (5.47 nm) than the control (2.8 nm). Following an O/N soak in water, both gels produced an optical blue shift equating to ~20% decrease of the magnitude relative to the initial shift resulting from gel infiltration. Since the % change in the magnitude of the blue shift following O/N water soak for the QD loaded gel is equivalent to the control, the origin of the decrease is consistent with osmotic equilibrium hydrogel swelling and out-diffusion of polymer monomers and not loss of encapsulated QD (Chatterjee et al., *J. Aerospace Eng.* 16:55-64 (2003), which is hereby incorporated by reference in its entirety). This data suggests that a 5 wt % polyacrylamide gel with 0.76 wt % cross-linker is sufficient to encapsulate anionic QD (−24 mV surface charge) with hydrodynamic radius of ~21 nm as predicted from Stellwagen, *Electrophoresis* 19(10):1542-47 (1998), which is hereby incorporated by reference in its entirety, and Holmes & Stellwagen, *Electrophoresis* 12:612-19 (1991), which is hereby incorporated by reference in its entirety.

TABLE 2

Optical Red Shifts (nm) Following Processing of Hybrid Optical Sensors.

| | Hydrogel | | Soak O/N in Water | | +TCEP (2 hr) + water rinse | |
|---|---|---|---|---|---|---|
| | Avg | Stdev | Avg | Stdev | Avg | Stdev |
| Cntrl | 2.80 | 0.16 | 2.30 | 0.78 | 1.207 | 0.328 |
| QD~8.9 uM | 5.47 | 0.45 | 4.51 | 0.56 | 1.814 | 0.418 |

These samples were then treated with TCEP disulfide reducing agent to break the BAC cross links, which were formulated at a 4:1 BAC:BIS mole ratio. Significant swelling is anticipated but the gel cannot completely dissolve due to the persistence of BIS cross links. Each hybrid gel sensor was soaked in 500 µL 50 mM TCEP for 2 hours and then rinsed with water. Optical shifts recorded following TCEP treatment revealed significant blue shifts for both gels with the QD gel exhibiting a larger % decrease due to loss of the high refractive index nanoparticles (NP). The residual red shifts following TCEP treatment for both gel samples were similar (not statistically different, p=0.05), which suggests efficient QD release. This data demonstrates that high refractive index NP can be used for optical amplification.

Using a bench-top Abbe refractometer, the refractive index of the 5 wt % polyacrylamide control hydrogel was measured to be $\eta=1.3459$. The refractive index of the QD loaded hydrogel was measured to be $\eta=1.3488$. It was estimated, assuming a QD loading level of 0.29% and a QD $\eta \sim 2.5$ (Imai et al., *Eu. Polymer J.* 45(3):630-38 (2009), which is hereby incorporated by reference in its entirety), that the refractive index of the bulk QD gel should be $\eta=1.3493$, which is only slightly higher ($\Delta=0.0005$) than what was experimentally measured. From knowledge of the sensor WSS (205 nm/RIU), the anticipated sensor red shift ($\Delta\lambda_r$) for gels in the porous sensor relative to water ($\eta=1.3333$) can be predicted. The control gel red shift was measured to be 2.30 nm after overnight water soak (see Table 2), as expected. For the same gel loaded with QD, the measured red shift after overnight water soak was 4.51 nm (see Table 2), which is a ~23% higher refractive index change. This demonstrates that high refractive index nanoparticles may be used to amplify the optical signal.

Discussion of Examples 1-4

The development of nanoporous silicon sensor design employing an optical amplification strategy was sought, to leverage the fact that PSi is a volume (porosity) sensitive transducer. The approach was to integrate a target responsive hydrogel (TRAP-gel) into the porous matrix of a PSi optical sensor (Bonanno & DeLouise, *Adv. Funct. Mater.* 20(4):573-78 (2010) (see Examples 5-16, infra); Bonanno & DeLouise, *Mater. Res. Soc'y Symp. Proc.* 1133:AA01-05 (2008); Bonanno & DeLouise, *Proc. SPIE* 7167:71670F (2009), each of which is hereby incorporated by reference in its entirety). Probe molecule analogues are covalently linked to the backbone of the hydrogel. Chains can be crosslinked by, for example, multivalent antibodies. Target competes for binding to the antibody causing crosslinks to break and consequent polymer swelling and chain dissolution. This strategy extends probe analogue throughout the 3-D internal volume of the pore volume improving upon techniques that limit probe immobilization to the internal rigid surface area (2-D) of PSi. Target induced material property changes (swell and mass loss) and the corresponding refractive index changes are significantly large for optical detection without signal amplification. Proof of principle of this sensor design concept employing polyacrylamide and amine-functionalized polyacrylamide/N-(3-aminopropyl)-methacrylamide (pAAm-NA) hydrogels have been demonstrated (Bonanno & DeLouise, *Adv. Funct'l Mater.* 20(4):573-78 (2010) (see Examples 5-16, infra); Bonanno & DeLouise, *Mater. Res. Soc'y Symp. Proc.* 1133:AA01-05 (2008); Bonanno & DeLouise, *Proc. SPIE* 7167:71670F (2009), each of which is hereby incorporated by reference in its entirety). To improve signal to noise, extend the lower limit of detection, and enable colorimetric read out by eye, an optical amplification strategy was developed by incorporating high refractive index nanoparticles (NP) into the hydrogel. NP have been incorporated into polymer films, as high as 50 wt %, to make highly transparent high RI films for various optical applications (Imai et al., *Eu. Polymer J.* 45(3):630-38 (2009); Lü et al., *J. Mater. Chem.* 13:2189-95 (2003), each of which is hereby incorporated by reference in its entirety). Studies show that the polymer RI scales linearly with NP wt % loading (Zimmermann et al., *J. Mater. Res.* 8(7):1742-48 (1993), which is hereby incorporated by reference in its entirety). In this sensor design, NP can be incorporated in different ways to tune the hydrogel target optical response. For example, NP can be nonspecifically encapsulated or surface functionalized to bind probe analogue directly on the polymer chain or to participate in forming chain cross-links Target binding will induce swelling that allows NP to diffuse out.

The data described in Examples 1-4 validate the viability of a NP optical signal amplification scheme employing hybrid porous silicon (PSi) sensors. The development of target responsive hydrogels integrated with PSi optical transducers was investigated. These hybrid-PSi sensors can be designed to provide a tunable material response to target concentration ranging from swelling to complete chain dissolution. The corresponding refractive index changes are significant and readily detected by the PSi transducer. To increase signal to noise, lower the limit of detection, and provide a visual read out capability, the incorporation of high refractive index nanoparticles (NP) into the hydrogel for optical signal amplification was investigated. These NPs can be nonspecifically encapsulated, or functionalized with bio active ligands to bind polymer chains or participate in cross linking Examples 1-4 demonstrate encapsulation of high refractive index QD nanoparticles into a 5wt % polyacrylamide hydrogel crosslinked with N,N'-methylenebisacrylamide (BIS) and N,N Bis-acryloyl cystamine (BAC). A QD loading (~0.29 wt %) produced a 2× larger optical shift compared to the control. Dissolution of disulphide crosslinks using TCEP reducing agent induced gel swelling and efficient QD release. It is believed that this hybrid sensor proof of concept demonstrates a versatile technology platform capable of detecting a wide range of bio/chemical targets. Target analogs can be linked to the polymer backbone and cross-links can be achieved with target responsive multivalent receptors, such as antibodies, using known attachment chemistry. The optical signal amplification scheme will enable a lower limit of detection sensitivity not yet demonstrated with PSi technology and, as demonstrated herein, colorimetric readout visible to the naked eye.

Example 5

Copolymer Synthesis

Procedures to copolymerize AAm with NAPMAAm were adopted from Seiffert and Oppermann, *Macromolec. Chem. Phys.* 208:1744-52 (2007), which is hereby incorporated by reference in its entirety, and details are reported in Bonanno & DeLouise, *Proc. SPIE* 7167:71670F (2009), which is hereby incorporated by reference in its entirety. In brief, AAm (MP Biomedical, MW=71.08 g mol$^{-1}$), NAPMAAm (Polysciences Inc., MW=178.7 g mol$^{-1}$), and sodium formate (HCOONa, Alfa Aesar, MW=68.01 g mol$^{-1}$) were added to deionized water (30° C., 15 minutes) and stirred under nitrogen. The total monomer concentration was fixed (4.6 mM in 10 ml water) and the exact monomer formulations are listed in Table 3. Chain transfer agent, HCOONa, was added to control the linear polymer chain length (Fevola et al., *J. Polym. Sci. A* 41:560-68 (2008), which is hereby incorporated by reference in its entirety). Free radical polymerization was initiated with N,N,N'N'-(Tetramethylethylenediamine) (0.25 mol %, 1.7 µl, Sigma, MW=116.2 g mol$^{-1}$) and ammonium persulfate (0.1 mol %, 70 µl of a 2wt % aqueous solution, Sigma). Precipitation in methanol (2 wt % hydrochloric acid) resulted in crude product that was filtered, washed in methanol, resolubilized in deionized water, and dialyzed against water (2 days at 4° C.) with stirring (Spectra/Por®, MWCO=3500 g mol$^{-1}$). Remaining solvent was removed via rotary evaporation and high vacuum for 24 hours. Characterization of the various copolymer products was completed by $^1$H NMR spectroscopy and size exclusion chromatography (SEC) as described in Bonanno & DeLouise, *Proc. SPIE* 7167:71670F (2009), which is hereby incorporated by reference in its entirety.

TABLE 3

Reaction Mixtures and Copolymer Product Characterization.

| Composition of Reaction Mixture [a] | | | | Characterization of Resulting Copolymer Products | | | | |
|---|---|---|---|---|---|---|---|---|
| Fraction of NAPMAAm Added [f, mol %] | [AAm] [mmol] | [NAPMAAm] [mmol] | [HCOONa] [mmol] | Fraction of NAPMAAm in copolymer [F, mol %] [b] | Mn [c] [g mol$^{-1}$] | Mw [c] [g mol$^{-1}$] | Polydispersity Mw/Mn | Rg [d] [nm] |
| 0 | 4.600 | 0 | 5 | — | — | — | — | — |
| 2 | 4.508 | 0.092 | 5 | 4.14 | 17400 | 63133 | 3.63 | 21.5 |
| 10 | 4.140 | 0.460 | 5 | 17.82 | 24900 | 95600 | 3.84 | 26.5 |
| 25 | 3.450 | 1.150 | 5 | 37.27 | 33278 | 143985 | 4.33 | 37.4 |

[a] Copolymerization of AAm with NAPMAAm with varying mole fractions of NAPMAAm (f) and fixed amount of sodium formate (HCOONa) added to monomer reaction mixture in 10 ml volume deionized water.
[b] F was determined using $^1$H NMR (400 MHz in D$_2$O) (Bonanno & DeLouise, *Proc. SPIE* 7167: 71670F (2009), which is hereby incorporated by reference in its entirety).
[c] Copolymer number average molecular weight (Mn) and weight average molecular weight (Mw) were determined using size exclusion chromatography (SEC).
[d] The radius of gyration (Rg) was calculated using dynamic light scattering. Rg is the root-mean-square distance of the elements in the chain from its center of gravity and describes the mean radius of the random coil polymer chains.

Example 6

Sulfhydryl Functionalization of Copolymer

Copolymer was dissolved in phosphate buffered saline buffer (PBS, pH 7.4, 10 wt %). SATP (Thermo Scientific, 2 µl of 1.533 M, MW=245.25 g mol$^{-1}$) diluted in dimethylformamide was added to 50 µl of copolymer solution (2 hours at room temperature). Unbound SATP was removed with dialysis (Harvard Apparatus, Dispo Equilibrium Dialyzer, MWCO=5000 g mol$^{-1}$) overnight at room temperature against 1000 excess volume of PBS. Hydroxylamine-HCl in PBS (5 µl of 1 M, pH 7.1) was added to 50 µl SATP-bound copolymer solution (mixed 1 hour at room temperature) to deprotect the acetylated sulfhydryl (SH) groups. Ellman's Assay (Riddles et al., *Anal. Biochem.* 94:75-81 (1979), which is hereby incorporated by reference in its entirety) was performed to quantify SH attachment to copolymer chains with varying mol % NAPMAAm (Table 4). Dimethylsulfoxide (DMSO) was added as an oxidizing agent (2 µl) to sulfhydryl functionalized copolymer solutions (50 µl of 10 wt %) to promote disulfide bond formation.

Example 7

PSi Sensor Preparation

The methods employed to produce PSi films have been described in detail in Bonanno & DeLouise, *Biosens. Bioelectron.* 23:444-48 (2007), which is hereby incorporated by reference in its entirety. Briefly, mesoporous PSi Bragg mirrors were fabricated from p+ <100> silicon wafers (B doped, 0.006-0.009 Ω-cm) using an electrochemical etch process at room temperature. Etching was completed in electrolyte containing ethanol (70%) and hydrofluoric acid (HF, 15%). The Bragg mirror consisted of 16 alternating layers of porosity (79 and 87%, d=19 and 43 nm, respectively) with a total thickness (~3.2 µm) measured by SEM. The wavelength shift sensitivity (WSS=308.6 nm/RIU) was determined using infiltration of liquids with known η values. The other PSi architectures studied in FIGS. 4A-D were fabricated using similar electrochemical etching techniques and their resulting pore characteristics are listed in Table 5. Macroporous PSi (d>50nm) was etched into n+ <100> silicon wafers (Sb doped, 0.01-0.08 Ω-cm) in electrolyte containing Pluronic L31 (0.1%) and HF (5%). After thermal oxidation (900° C., 3 minutes) all PSi sensors were silanized with (mercaptopropyl)trimethoxysilane (2 wt %, Gelest) in ethanol (50%) for 15 minutes, rinsed with ethanol, rinsed with water, dried with

TABLE 4

Characterization of AAm/NAPMAAm Copolymers and Sulfhydryl Functionalized Copolymers.

| Fraction of NAPMAAm in reaction solution, f [mol %] | Fraction of NAPMAAm in Copolymer [a], F [mol %] | Copolymer Mn [b] [g/mol] | Calculated Quantity of NAPMAAm [nmoles] | Quantitiy of Attached Sulfhydryl Groups to Copolymer [c] [nmoles] | Ratio of Sulfhydryl Concentration Present to Available NAPMAAm Moieties |
|---|---|---|---|---|---|
| 2 | 4.14 | 17400 | 1.19 | 7.53 | 6.33 |
| 10 | 17.82 | 24900 | 3.58 | 26.50 | 7.41 |
| 25 | 37.27 | 33278 | 5.60 | 34.30 | 6.13 |

[a] mol % NAPMAAm was determined using $^1$H NMR (Bonanno & DeLouise, *Proc. SPIE* 7167: 71670F (2009), which is hereby incorporated by reference in its entirety).
[b] Copolymer number average molecular weight (Mn) and weight average molecular weight (Mw) were determined using size exclusion chromatography (SEC).
[c] Quantity of attached sulfhydryl groups was determined using colorimetric Ellman's Assay.

nitrogen gas, and kept at 100° C. for 20 minutes to cross-link the silane and evaporate any remaining solvent.

TABLE 5

Characterization of PSi Sensor Architectures.

| | | Etching Conditions | | | Characterization of Porous Structure | | | |
|---|---|---|---|---|---|---|---|---|
| | | | | | Average | | | Liquid |
| Doping Type | Architecture | Current Density [mA cm$^{-2}$] | Etch time [s] | Depth [μm] | Pore diameter [a] [nm] | Gravimetric Porosity [%] [b] | WSS [c] [Δλ/ΔRIU] | Infiltration Porosity [%] [d] |
| p | Single Layer | 30 | 143.8 | 1.68 | 19 | 79 | 287.1 | — |
| p | Single Layer | 60 | 94.4 | 1.68 | 43 | 87 | 393.9 | — |
| n | Single Layer | 40 | 120.0 | 1.68 | 73 | 78 | 218.1 | — |
| n | Single Layer | 70 | 108.0 | 1.68 | 106 | 92 | 328.2 | — |
| p | Mirror | 30/60 | 4.01/3.03 × 16 | 3.20 | 19/43 | 79/87 | 308.6 | 64.2/73.5 |
| n | Mirror | 40/70 | 3.75/2.75 × 16 | 2.88 | 73/106 | 78/92 | 231.5 | — |

[a] Image J software analysis of top down SEM images were used to calculate the average pore diameter within a distribution.
[b] Gravimetric measurements calculate % porosity based on mass measurements as described in Equation 1. The Si chip mass is measured prior to (m1) and post etching of a porous Si layer for 300 seconds (m2). The porous Si layer is dissolved away in basic KOH and the final mass (m3) is measured.

$$\text{Equation 1} \quad P = \frac{m1 - m2}{m1 - m3} \times 100$$

[c] Wavelength shift sensitivity (WSS) is measured by measuring the wavelength shift associated with filling the pores with fluids of known η. Plotting wavelength shift versus change in η results in a linear plot with slope indicating the WSS (Δλ/Δη).
[d] Bruggeman approximation theory is utilized in MATLAB to simulate porous Si sensor response. Input values of porous layer depth are held constant and the porosity values are calibrated to attain the same response as observed in experimental measuring of WSS for filling pores with solutions of known η. The porosity values attained in simulation represent the open porosity available for liquid infiltration as described in Segal et al., *Adv. Funct'l Mater.* 17:1153-62 (2007), which is hereby incorporated by reference in its entirety, and are often lower than those measured by gravimetric measurements.

Example 8

Preparation of S—S-coPAAm-PSi Hybrid Sensor

The sulfhydryl functionalized copolymer solutions prepared as described in Examples 5-6 were immediately applied to the mercaptosilane treated PSi sensors in a custom glass fixture within a humidified chamber to minimize thickness of polymer on top of the PSi sensor (700 μm). Disulfide bond formation (cross-linking of the hydrogel) was allowed to continue at room temperature in the humidified chamber for 6 days, as Ellman's Assay (Riddles et al., *Anal. Biochem.* 94:75-81 (1979), which is hereby incorporated by reference in its entirety) results indicated complete disulfide formation occurs within 5 days (FIGS. 5A-B) (see Example 10, infra). The resulting hybrid S—S-coPAAm-PSi sensors were soaked in deionized water (10 ml) for 2 days on a shaker plate (water replaced after 1 day) to allow equilibrium swelling and release of uncross-linked copolymer chains.

Example 9

Optical Detection of Reflectance Spectra

The hybrid S—S-coPAAm-PSi sensors were held within a custom fixture and exposed to a normal incident beam of white light (spot size ~1.3 mm$^2$). Reflectance spectra normal to the surface were measured using an Advantes 3648-USB2 spectrophotometer (optical resolution of 0.06 nm pixel$^{-1}$). The custom fixture holds the PSi sensor in a well containing various solutions and is covered by glass to diminish solution evaporation. All error bars in plots represent the standard deviation of each data point taken with a minimum of n=2 for interday experiment trials and 3 measurement locations per sensor.

Example 10

Ellman's Reagent to Quantify Free Sulfhydryl Concentration in Solution

Ellman's reagent, 5,5'-dithio-bis-(2-nitrobenzoic acid) (DTNB), is a versatile water-soluble compound used to quantitate free sulfhydryl (SH) groups in solution (Riddles et al., *Anal. Biochem.* 94:75-81 (1979), which is hereby incorporated by reference in its entirety). A measurable yellow-colored product results when this chemical reacts with SH groups. A calibration curve was created by adding 30 μl of varying concentrations of cysteamine to 95 μl of 0.1 mM DTNB aqueous solution (pH 7.1) and measuring the absorbance at 405 nm (FIG. 5A). SH attachment to various copolymer formulations (0-37.27 mol % NAPMAAm) after SATP chemistry was performed was determined by comparing absorbance measurements to the calibration curve. As disulfide bonds form between SH functional copolymer chains the number of free SH groups decreases. This reduction of SH concentration was temporally monitored to determine how long complete disulfide cross-linking of the S—S-coPAAm hydrogel network takes (FIG. 5B). Copolymer solution (30 μl, 4.14 mol % NAPMAAm) was added. The [SH] decreases and saturates by 5 days for the copolymer solution. All S—S-coPAAm hydrogels were therefore allowed to cross-link for 6 days in a humidified chamber before subsequent use.

Example 11

Synthesis of Disulfide Cross-Linked Hydrogel (S—S-coPAAm)

Chemical formation of S—S-coPAAm is shown in FIGS. 6A-F. Free radical polymerization of acrylamide (AAm) and N-(3-aminopropyl)-methacrylamide (NAPMAAm) monomers formed copolymer chains with a controlled concentration of nucleophilic amine moieties (FIGS. 6A-B) (Bonanno & DeLouise, *Mater. Res. Soc'y Symp. Proc.* 1133: AA01-05 (2008); Bonanno & DeLouise, *Proc. SPIE* 7167: 71670F (2009); Seiffert & Oppermann, *Macromolec. Chem. Phys.* 208:1744-52 (2007), each of which is hereby incorporated by reference in its entirety). Reaction with N-Succinimidyl-S-acetylthiopropionate (SATP) adds protected sulfhydryl groups to the copolymer chains. The NHS-ester present in the SATP molecule reacts with primary amines to form stable amide bonds (FIG. 6C). The sulfhydryl groups were subsequently deprotected by hydroxylamine (FIGS. 6D-E) and cross-links between copolymer chains resulted upon formation of disulfide bonds (FIG. 6F) producing a hydrogel network. Addition of TCEP reducing agent cleaves the cross-links inducing hydrogel dissolution.

Characterization by $^1$H NMR spectroscopy proved that increasing the molar ratio of NAPMAAm to AAm in the pre-polymer solution resulted in sequentially more amine moieties in the copolymer chains (Table 3) (Bonanno & DeLouise, Proc. SPIE 7167:71670F (2009), which is hereby incorporated by reference in its entirety). Reaction chemistry for cross-linking is specific to the amine moieties. Therefore, varying the mol % NAPMAAm in the copolymer backbone controls the cross-linking ability of the copolymer chains. As cross-linking density increases, swelling is restricted and the $\eta$ of the resulting hydrogel increases. Visual increases in rigidity of the formed hydrogels were also observed as the mol % NAPMAAm was increased (4.14, 17.82, and 37.27%, (FIG. 7)). The negative control (0 mol % NAPMAAm copolymer) did not form a hydrogel but remained in solution phase as expected.

A bench-top Abbe refractometer (Bausch and Lomb) was used to measure the $\eta$ of each bulk hydrogel sample produced. Samples were first incubated in deionized water for 2 days on a shaker plate to allow for equilibrium swelling and uncross-linked copolymer chains to diffuse out. A direct linear relationship between mol % NAPMAAm and $\eta$ values was observed (FIG. 8A). The optical response of the PSi Bragg mirror was used to analyze hydrogel infiltration into the porous matrix. Sulfhydryl functional copolymers in solution (10 wt %) were added to PSi Bragg mirrors that were functionalized with 3-(mercaptopropyl)trimethoxysilane (mercaptosilane) as described in detail in Examples 5-8. The mercaptosilane coating enables the copolymer chains to cross-link via disulfide bonds to the PSi substrate. Chemically tethering the hydrogel to the PSi produces reproducible optical responses that vary systematically with hydrogel composition (Bonanno & DeLouise, Proc. SPIE 7167:71670F (2009), which is hereby incorporated by reference in its entirety). Changes in $\eta$ of the PSi sensor resulting from addition of mercaptosilane and hydrogel (after soaked in water for 2 days) can be seen as wavelength shifts in the spectral peak in FIG. 8B. The wavelength shift for water ($\eta$=1.333) filling the pores is also shown as a reference spectrum to illustrate the additional shift attributed to cross-linked polymer fibers of the hydrogel.

Wavelength shift magnitude resulting for S—S-coPAAm hydrogels with varying mol % NAPMAAm cross-linked in the PSi Bragg mirror are shown in FIG. 8C. As mol % NAPMAAm is increased a red wavelength shift is observed, which is consistent with an increase in $\eta$ of the resulting hydrogel confined in the PSi. As expected, a 0 mol % NAPMAAm negative control polymer solution (100% AAm, 10 wt %, $\eta$=1.3455) produced no detectable wavelength shift beyond that observed for water ($\eta$=1.333) filling the pores. Here, polymer chains lack reactive amine moieties for sulfhydryl conversion and thus uncross-linked chains washed away during the 2 day soak period.

The wavelength shift for each hydrogel filling the PSi sensor was theoretically predicted using Bruggeman effective-medium approximation (Vinegoni et al., "Porous Silicon Microcavities," in 2 SILICON-BASED MATERIALS AND DEVICES 122-88 (Hari Nalwa ed., 2001), which is hereby incorporated by reference in its entirety. Pores were simulated to be filled 100% with materials of $\eta$ equal to what was measured on the bulk hydrogels (4.14, 17.82, 37.27 mol % NAPMAAm) using a bench-top Abbe refractometer and $\eta_{water}$=1.333 was used for 0 mol % NAPMAAm control (FIG. 8C). Simulation parameter values of thickness and open porosity of the PSi layers (Table 5) were determined by scanning electron microscopy (SEM, thickness only), gravimetry, and optical measurements as previously described in Segal et al., Adv. Funct'l Mater. 17:1153-62 (2007), which is hereby incorporated by reference in its entirety. Simulation and experimental results correlate within 1 standard deviation for each polymer tested (FIG. 8C). This optical measurement data demonstrates that the cross-linked hydrogel fills the 3-D PSi matrix. Stability of the fully hydrated hybrid sensors (in 1 ml water) was optically monitored for 48 hours. No observable wavelength shift was detected for any of the samples (0, 4.14, 17,82, 37.27 mol % NAPMAAm), indicating that the state of the composite hydrogel-PSi material is stable over this period. Initial testing indicates that dry storage (1 month) of the hybrid hydrogel-PSi devices and rehydration before use facilitated reproducible results. This is consistent with previous work of hydrogel-supported PSi sensors (DeLouise et al., Adv. Mater. 17:2199-203 (2005), which is hereby incorporated by reference in its entirety).

Example 12

Investigation of System Factors that Govern Sensor Temporal Response

Alternate forms of disulfide cross-linked hydrogels have previously been used as a proof-of-concept for integrating chemical-responsive hydrogels into microfluidic sensor systems (Sridharamurthy et al., Meas. Sci. Technol. 18:201-07 (2007); Chatterjee et al., Aerosp. Engrg. 16:55-64 (2003), each of which is hereby incorporated by reference in its entirety). In each case, a disulfide containing cross-linker (cystaminebisacrylamide, BAC) was used to form polyacrylamide hydrogels inside microchannels (diameter, d~hundreds of nm). Addition of reducing agents under flow conditions caused gel dissolution. Three important design parameters were highlighted: 1) outside concentration of target molecule, 2) original volume of the hydrogel, 3) cross-linking density of the hydrogel (Chatterjee et al., Aerosp. Engrg. 16:55-64 (2003), which is hereby incorporated by reference in its entirety). Important differences in the present design include: different hydrogel structure (disulfide cross-linking of preformed copolymer chains), confinement of hydrogel into smaller PSi pores (d~tens of nm) that have one inlet/outlet, and static (no flow) conditions. The aforementioned design parameters were investigated individually as they pertain to the present sensor system (see FIGS. 4A-D).

After TCEP analyte diffuses into the hydrogel-filled PSi matrix a small positive wavelength shift can be observed, correlating to the increased $\eta$ of the TCEP solution (Table 6). Within seconds the hydrogel begins to dissolve causing a wavelength blue shift as uncross-linked copolymer chains diffuse out of the PSi matrix. All wavelength shift data in FIGS. 4A-D are displayed in reference (0 on x-axis) to the reflectance peak position with water filling the PSi matrix. As demonstrated in Examples 1-4, incorporation of nanoparticles into the polymer matrix would enhance the wavelength shift.

TABLE 6

Refractive Iindex of TCEP Solutions Measured on a Bench-Top Abbe Refractometer (Bausch & Lomb, Series 512).

| TCEP Solution Concentration [mM] | Refractive Index, $\eta$ |
|---|---|
| 0 | 1.3330 |
| 1 | 1.3331 |
| 10 | 1.3349 |
| 50 | 1.3368 |
| 100 | 1.3502 |

Example 13

Effect of Hydrogel Structure on Observed Dissolution Response

Cross-linking density is shown to greatly affect hydrogel dissolution in FIG. 4A. Measurements were taken in a 1 ml bath of 50 mM TCEP for all cases. The negative control (0 mol % NAPMAAm) displays a wavelength red shift of 0.98 nm. This value correlates well with simulation for the increase in η of the TCEP solution (η=1.3368) entering the pores compared to water ($\eta_{water}$=1.333). No additional shift due to polymer is observed, because no amine moieties exist in the polymer backbone to allow sulfhydryl attachment or subsequent cross-linking Moreover, no temporal response shows that the PSi sensor is stable in the TCEP solution over the test interval.

Samples that formed hydrogel networks (4.14-37.27 mol % NAPMAAm, FIG. 4A) displayed an increased rate of wavelength blue shift response to TCEP with lowering cross-linking density. This demonstrates that less cross-linked hydrogels break apart and diffuse out of the PSi matrix more quickly. With higher cross-linking density, more entanglement of copolymer chains is probable and more disulfide bonds must break to free the chains. For the highest cross-linked sample (37.27 mol % NAPMAAm) only a small decrease in wavelength shift was observed even after 4-hour incubation in >100 mol excess of TCEP (5E-5 mol). Quantification of sulfhydryl groups on the pre-copolymer chains (5.49E-8 mol) was performed with an Ellman Assay (Table 4) (Riddles et al., Anal. Biochem. 94:75-81 (1979), which is hereby incorporated by reference in its entirety). This result is consistent with literature that reports similarly high concentrations of reducing agents (0.1-1 M) were needed to dissolve disulfide cross-linked hydrogels (0.273-0.682 mol % BAC cross-linker) over similar time periods (Sridharamurthy et al., Meas. Sci. Technol. 18:201-07 (2007); Chatterjee et al., Aerosp. Engrg. 16:55-64 (2003), each of which is hereby incorporated by reference in its entirety). One key difference observed with the present sensor system is that the wavelength shift never returns to zero (water filling the pores) even after overnight soaking in 0.1 M TCEP and subsequent rinsing with water. This indicates that residual polymer remains in the PSi, which is discussed in Example 15.

Example 14

Dissolution Response Dependence on the Concentration of Applied Target Analyte

The sensor system response was shown to also depend greatly on the concentration of TCEP (FIG. 4B). Measurements were taken on 4.14 mol % NAPMAAm hydrogels cross-linked into PSi Bragg mirrors mounted inside a 500 µl bath with varying TCEP concentrations (0-100 mM). The negative control (water only) showed no response whereas a wavelength blue shift was observed for all concentrations of TCEP tested (1-100 mM). The magnitude and rate of the response increased with TCEP bath concentration for 1-50 mM solutions. Both 50 mM and 100 mM TCEP solutions resulted in similar response, indicating that dissolution of the hydrogel is the limiting factor. As TCEP is noted for its fast diffusion and reactivity, chain disentanglement has previously been highlighted as the rate-limiting step for disulfide cross-linked hydrogel dissolution (Chatterjee et al., Aerosp. Engrg. 16:55-64 (2003), which is hereby incorporated by reference in its entirety). The experiments described in Examples 5-10 were performed in static solutions and future work may investigate how mixing improves dissolution kinetics.

Example 15

PSi Transducer Architecture Effects on Confined Hydrogel Dissolution

Examples 5-16 particularly investigated how confinement of the hydrogel inside the PSi volume affected dissolution. Results by Segal et al. show that pore size and porosity strongly influenced the extent and rate of the optical response reporting the phase transition behavior of a thermoresponsive hydrogel (poly(N-isopropylacrylamide) confined within a single layer porous $SiO_2$ template (Segal et al., Adv. Funct'l Mater. 17:1153-62 (2007), which is hereby incorporated by reference in its entirety). Therefore, the effects of pore diameter (d) and porosity (P) in single layer PSi films as well as Bragg mirror architectures comprised of alternating high and low porosity (large and small pore diameter) layers (FIG. 4C) (Vinegoni et al., "Porous Silicon Microcavities," in 2 SILICON-BASED MATERIALS AND DEVICES 122-88 (Hari Nalwa ed., 2001), which is hereby incorporated by reference in its entirety) were investigated. TCEP concentration (500 µl, 50 mM) and hydrogel cross-linking (4.14 mol % NAPMAAm) were kept constant. Data in FIG. 4C and FIG. 4D are normalized to the initial wavelength shift value attained with hydrogel filling the pores for each sensor investigated. This allowed for easier comparison between different PSi architectures as they display different wavelength shift sensitivity to changes inn (Table 5) (Vinegoni et al., "Porous Silicon Microcavities," in 2 SILICON-BASED MATERIALS AND DEVICES 122-88 (Hari Nalwa ed., 2001), which is hereby incorporated by reference in its entirety).

The influence of PSi sensor architecture on the incorporated hydrogel dissolution is evident in FIG. 4C. Dissolution includes three sequential phases: disentanglement of copolymer chains, dissolution of copolymer chains, and convective mass transport out of the PSi matrix (Chatterjee et al., Aerosp. Engrg. 16:55-64 (2003), which is hereby incorporated by reference in its entirety). The overall dissolution rate is determined by the slowest phase. The rate and saturating magnitude of the optical response decreased as pore diameter (d) was decreased in the single layers. This indicates that smaller pores restrict dissolution. In both cases, mirrors created from alternating porous layers (d=19/43 and 73/106 nm) displayed slower rates and smaller magnitudes of response than single layers of the same pore sizes. It is believed that irregular geometries existing at the interface between layers contributes to hindered disentanglement and/or diffusion. Porosity does not seem to have as large of an effect on dissolution as pore size displays. This is evident by the fact that similar porosity single layers with different pore sizes exhibit different behavior (FIG. 4C). A single time point at 4 hours of incubation in TCEP is displayed for each of the investigated PSi architectures (FIG. 4D). A strong inverse linear dependence between average pore diameter and dissolution in single layer PSi sensors is shown. Again, it can also be seen that mirrors illustrate slightly higher amounts of polymer remaining (residual wavelength shift) in the PSi matrix than single layers with similar average pore diameter.

Example 16

Colorimetric Detection of Target Analyte in Solution

Figure 9A:
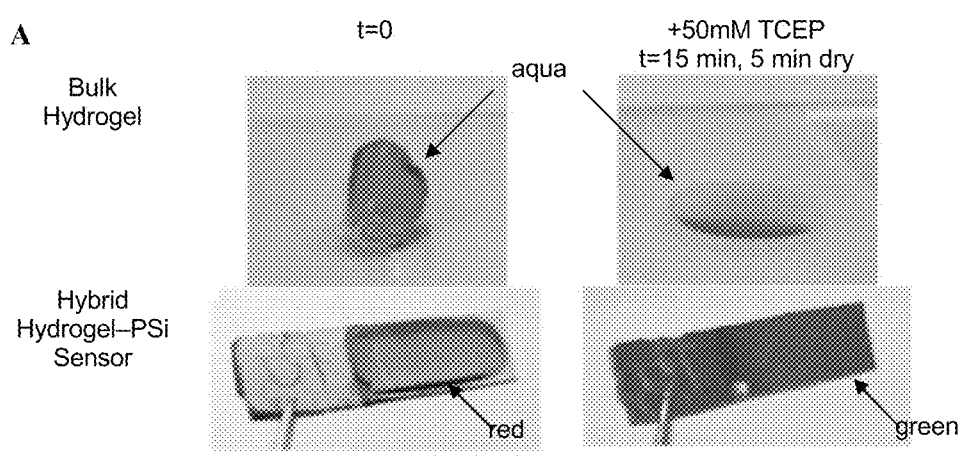
FIGS. 9A-B relate to the visual color readout of hybrid hydrogel-PSi sensors upon drying.
Figure 9B:
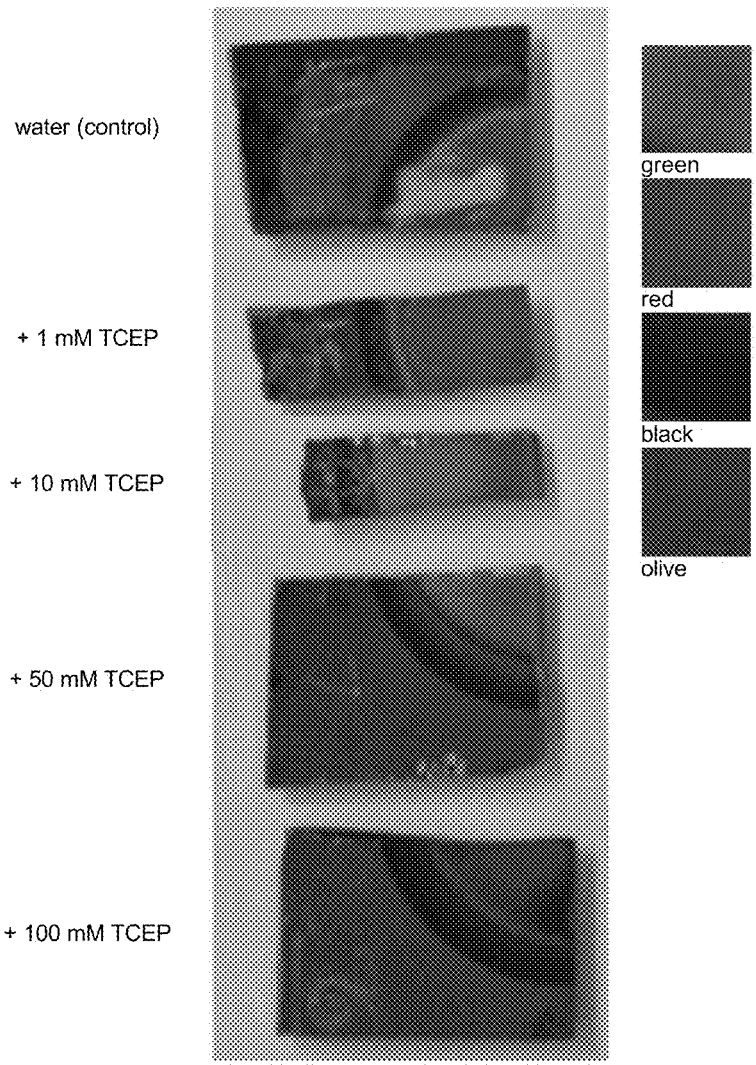
Figure 10:
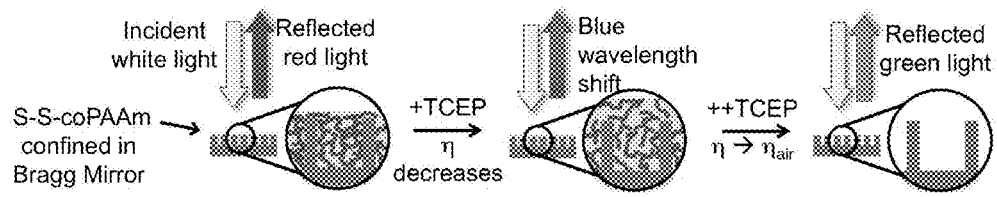
FIG. 10 is a schematic illustration of optical detection using a hybrid chemical-responsive hydrogel-porous Si sensor. Addition of target analyte, TCEP, breaks disulfide cross-links in the hydrogel (S—S-coPAAm) causing a decrease in refractive index that is optically detected by blue wavelength shifts in the reflectance spectrum. Addition of sufficient TCEP results in gel dissolution and large enough shifts in reflected light to visually observe color change by eye.

Visual detection of TCEP by the unaided eye was achieved with the exemplary hydrogel-PSi sensor system by color readout (FIGS. 9A-B). Pictures of bulk S—S-coPAAm hydrogel (4.14 mol % NAPMAAm) are contrasted to pictures of the same S—S-coPAAm cross-linked into a PSi Bragg mirror (d=19/43 nm) prior and post exposure to TCEP (FIG. 9A). A visual color change from red to green in the PSi sensor is evident after a 15 minute soak in TCEP (500 µl, 50 mM) on a shaker plate, subsequent rinsing with water, and 5 minute air-drying on the bench-top. In contrast to the wet measurements shown in FIGS. 4A-D, the dry measurements taken here resulted in a large wavelength blue shift (>100 nm) of the peak reflected light. This corresponds to sufficient dissolution of hydrogel from the PSi matrix to prevent retention of water inside the internal pore volume resulting in the loss of water from the PSi matrix in addition to copolymer. A dilution series of TCEP concentration (0-100 mM) shows that the initiation of color change is dependent on applied TCEP concentration (FIG. 9B). For exposure to TCEP>10 mM a complete visual color change from red to green is evident. See also FIG. 10.

Discussion of Examples 5-16

Examples 5-16 describe a hydrogel synthesis strategy based on amine functionalization of the otherwise chemically inert polyacrylamide. The amine groups allow incorporation of versatile reaction chemistries enabling the control of cross-links between copolymer chains based on complimentary target-probe systems. Examples 5-8 demonstrate the incorporation of a model chemical-responsive hydrogel into a 1-D photonic PSi sensor to achieve tunable direct optical detection. Disulfide chemistry was incorporated to control cross-linking of this hydrogel system within a PSi Bragg mirror sensor. Changes in η of a disulfide cross-linked hydrogel (S—S-coPAAm) incorporated into a PSi Bragg mirror were monitored upon exposure to a target reducing agent analyte (Tris(2-Carboxyethyl)phosphine (TCEP)). Fabrication of a PSi Bragg mirror involved anodic electrochemical etching of a p-type, boron-doped Si wafer (Vinegoni et al., "Porous Silicon Microcavities," in 2 SILICON-BASED MATERIALS AND DEVICES 122-88 (Hari Nalwa ed., 2001), which is hereby incorporated by reference in its entirety). Control of the applied current was used to create alternating layers of high and low porosity to dictate the frequency of a distinct peak in the white-light reflectivity spectrum. TCEP-induced dissolution of the S—S-coPAAm hydrogel resulted in decreasing η. Large η changes resulted in visual color response that could be observed by the unaided eye. Direct optical monitoring of a characteristic peak in the white light reflectivity spectrum of the incorporated PSi Bragg mirror facilitates real-time detection of the hydrogel dissolution in response to target analyte (reducing agent) over a time scale of minutes. The dissolution characteristics of the S—S-coPAAm hydrogel were shown to depend on hydrogel cross-linking density and the applied target analyte concentration. Additionally, effects due to responsive hydrogel confinement in a porous template were shown to depend on pore size and architecture of the PSi transducer substrate. This hybrid design exhibits characteristics optimal for POC chemical and/or biological sensing due to its inexpensive fabrication, straightforward optical detection, and capability for visual color readout without any secondary label amplification.

The disulfide linked hydrogel system described in Examples 5-16 serves as a further proof-of-concept for integrating chemical-responsive hydrogels into nano-structured PSi sensors. One advantage of this sensing system is the capability for direct visual color readout (1 hour assay time and 5 minute drying time) in addition to the capability for more precise temporal monitoring with reflectance spectrometry. While Examples 5-16 specifically report on optical detection of the dissolution response of a disulfide cross-linked hydrogel in response to TCEP, which is well known, the disulfide crosslinking of this copolymer system is unique and the optical detection of dissolution based on refractive index changes of the nano-confined responsive hydrogel is demonstrated herein. The effects of nano-scale confinement of hydrogel dissolution properties are also demonstrated. This hybrid material system remains low-cost and proves to be easily translatable for POC sensing. It is expected that biologically relevant probe-target interactions can be incorporated onto the amine-functionalized copolymer backbone described in Examples 5-16 to create crosslinked hydrogel networks, and that introduction of nanoparticles into the matrix will further enhance the sensitivity of these devices.

Example 17

Gel Formation

Polyacrylamide/N-(3-aminopropyl)-methacrylamide random copolymers that varied in amine mole fraction (0-25%) have previously been synthesized and characterized (NMR, size exclusion gel chromatography, custom protocols developed in the lab) (Bonanno & DeLouise, Proc. SPIE 7167:11 (2009), which is hereby incorporated by reference in its entirety). Sodium formate chain transfer agent was used to control polymer chain length and reactions were terminated at low conversion. Typical number average molecular weights ($M_n$) range between 15-20 kDa and polydispersities of 2-3. The amines provide functional sites to attach bioactive groups to induce cross-links. Hydrogels (FIG. 11) were formed using (A) glutaraldehyde to directly cross-link the amines (Bonanno & DeLouise, Proc. SPIE 7167:11 (2009), which is hereby incorporated by reference in its entirety), (B) disulphides (through modification of amines to sulfhydryls) (Bonanno & DeLouise, Adv. Funct. Mater. 20:1-6 (2010); Bonanno & DeLouise, Adv. Funct'l Mater. 20(4):573-78 (2010) (see Examples 5-16, supra), each of which is hereby incorporated by reference in its entirety;), and (C) biotin-streptavidin (SA) interactions. In the glutaraldehyde studies, it was determined that a minimum of 4 wt % solids was needed to observe gel formation. In the SA system, the copolymer (17.5 mol % NAPMAAm by 1H NMR) was biotinylated with amine reactive sulfo-NHS-LC-Biotin (Pierce). Studies were conducted to determine the SA concentration needed to form hydrogels. SA was added to a copolymer solution by varying the molar ratio of SA:amines between 1.4 to 0.1 resulting in a 5 wt % solution. SA is a multivalent cross-linker with four biotin binding sites. In this series the number of SA biotin binding sites to biotin (assuming all amines were biotinylated) varied from 24:5, 3:1, 2:1, 1:1, 4:10. Gel formation required that SA binds biotin on at least two different chains, forming crosslinks. It was observed that samples with biotin binding sites:biotin ratio of 3:1, 2:1, and 1:1 formed gels, while the higher and lower ratio samples did not noticeably increase in viscosity. Presumably at low SA concentration the cross-link density was too low and at high concentration SA molecules did not bind biotin on different chains.

In addition to the above, hydrogel formation was investigated in systems more pertinent to construction of the commercially useful optical sensors. Specifically, 1-ethyl-3-(3-dimethylaminopropyl) carbodiimide (EDC) was utilized to couple the glucuronide side chain of M3G (FIG. 12) to the amines on the co-polymer chains (8.1 mol % NAPMAAm) using a 2 molar excess of M3G to amines. M3G attachment was confirmed by NMR and size exclusion chromatography. Coupling efficiency has not yet been rigorously determined, but an average increase in $M_n$ of ~6000 following M3G attachment was measured. After dialysis, cross-linking the purified M3G-functionalized copolymer was attempted by direct addition of α-MAb solution with a stoichiometric 1:2 antibody to amine molar ratio (assuming 100% M3G coupling efficiency). The reaction proceeded at room temperature for 4 hours on a shaker plate, and was subsequently moved into 4° C. for a longer incubation period. After 7 days no visible sign of gel formation was noted. To this solution was added Protein G (Sigma, MW=21,600 g mol$^{-1}$) in a 1:2 molar ratio of Protein G:antibody because there are 2 antibody $F_c$ binding sites per Protein G. Successful formation of stiff hydrogels resulted within hours (FIG. 13A) (see FIG. 2 (Protocol 2)). These gels withstood cycles of dehydration and rehydration (FIGS. 13A-B). The fully hydrated gels had sufficient mechanical integrity (unquantified) that prevented uptake into a pipet. Preincubation of Protein G with free antibody (1:2 molar ratio) also resulted in gel formation when added to M3G functionalized polymer chains (see FIG. 2 (Protocol 3)) provided that the total solids exceeded 4 wt %. These findings indicate the possible importance of cross-linker length and avidity. As a first attempt to determine whether Protein G assisted gels were responsive to target, a high concentration of M3G (8.67 mM) in PBS solution was introduced. After application of the M3G, the solution was mixed with a pipette for 1 minute and the gel was observed to remain in a solid state (FIG. 13C). After incubation in a humidified chamber for 15 minutes, mixing again with a pipette resulting in dissolution of the gel to a viscous solution, as evidenced by the presence of bubbles that could be easily taken up by a pipette (FIG. 13D). This indicates that biomolecular responsive T-gels can be synthesized.

Example 18

Hybrid Sensor Formation

Figure 14:
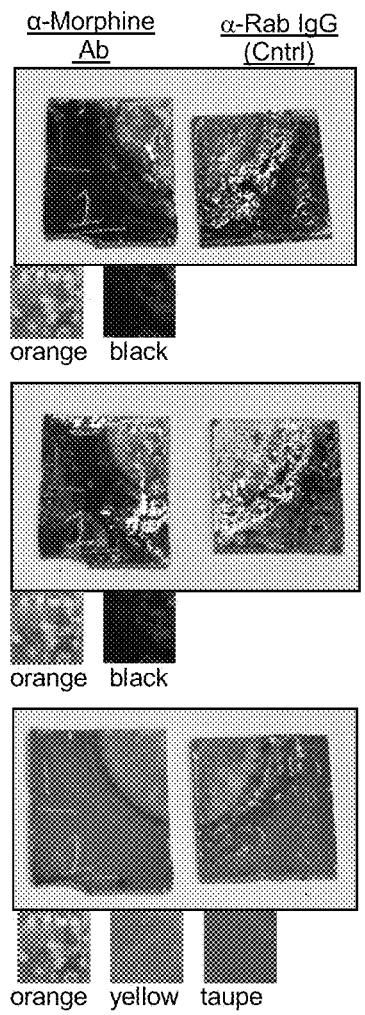
FIG. 14 shows a hybrid photonic sensor with visual readout capability. An opiate responsive T-gel and aR-Ab control gels were cross-linked directly in a macroPSi sensor. After exposure to M3G target, only the T-gel sensor produced a color response upon drying.

Polyacrylamide, glutaraldehyde, disulphide, and M3G-based gels were successfully crosslinked directly into PSi sensors and studies proved the optical sensor could detect small changes in η due to gel swelling and wt % gel solids (Bonanno & DeLouise, *Proc. SPIE* 7167:71670F (2009); Bonanno & DeLouise, *Adv. Funct. Mater.* 20(4):573-78 (2010) (see Examples 5-16, supra); Bonanno & DeLouise, *Mater. Res. Soc'y Symp. Proc.* 1133:AA01-05 (2008), each of which is hereby incorporated by reference in its entirety). Disulphide gels were responsive to presence of chemical reducing agent (Tris(2-carboxyethyl)phosphine hydrochloride, TCEP) and within 15 minutes dissolved to produce a visual color change when the sensor was dried. It was shown that the TCEP concentration required to dissociate the gels was positively correlated with cross-link density (Bonanno & DeLouise, *Adv. Funct. Mater.* 20:1-6 (2010); Bonanno & DeLouise, *Adv. Funct'l Mater.* 20(4):573-78 (2010) (see Examples 5-16, supra), each of which is hereby incorporated by reference in its entirety). Proof of principle studies were also successful at cross-linking the M3G responsive T-gels described in Example 17 directly into PSi sensors (FIG. 14). In this Example, a control gel was formed by adding Rabbit IgG and Protein G to M3G coupled polymer chains. The control gel did not swell or appear as optically clear as the T-gel, and exposure to free M3G caused gel dissolution of the αM-Ab gel only. After drying, the PSi sensor changed color (orange to yellow) due to dissolution of the polymer chains causing a large Ti change (~100 nm), whereas the control chip remained orange as the porous matrix remained filled with dehydrated polymer. The specific color change reported is customizable and determined by design of the optical sensor.

Example 19

Integrate T-Gel with PSi Optical Sensor

T-gels will be crosslinked directly into macroPSi sensors (pore diameter 50-150 nm) fabricated as previously described (DeLouise & Miller, *Proc. SPIE* 5357:111-25 (2004); Ouyang et al., *Anal. Chem.* 79(4):1502-06 (2007); Ouyang et al., *Appl. Phys. Lett.* 88:163108 (2006); Ouyang et al., *Proc. SPIE* 5511:71-80 (2004), each of which is hereby incorporated by reference in its entirety). Application of the T-gel to the PSi sensor will be performed via spin coating to precisely control and minimize the thickness of the gel layer above the sensor matrix (FIG. 15A). This is optimal for two reasons. First, target must diffuse through this gel layer before entering the sensor matrix where the signal is transduced. At low target concentrations, a thick gel layer on top of the sensor will inhibit target detection and may give rise to false negatives. Second, a thick layer will also delay target diffusion into the porous sensor, which will translate to slower sensor response times.

Spin coating (UR Chemistry Dept) was used to cast thin gel precursor solutions on silicon wafers. After gel formation and equilibrium swelling, ellipsometry was used and it was observed, as expected, that spin speed and gel thickness are inversely related (FIG. 15B). It was proven that gels cast onto sensor cross-link throughout the porous matrix by comparing the magnitude of the wavelength shift measured with theoretical estimates calculated by filling the porous matrix with a substance equal to the bulk gel refractive index (FIG. 15C). These same spin coating techniques will therefore be used to optimize PSi optical sensor function.

Example 20

Transfer of Organic Soluble Quantum Dots into Water

Ligand exchange procedures to transfer organic soluble QD into water using dihydrolipoic acid (DHLA) and cysteamine were developed as described in Table 7 (DHLA) and Table 8 (cysteamine).

TABLE 7

Transfer of TOPO/ZnS Coated CdSe QDs into Water with DHLA.

(1) Added 50 μl of freshly prepared dihydrolipoic acid (DHLA) and 1 ml MeOH, mixed.
(2) The pH of the solution was adjusted to 11 with tetramethylammonium hydroxide pentahydrate ($(CH_3)_4NOH \cdot 5H_2O$).
(3) 0.5 ml (0.65 mg) TOPO-capped CdSe/ZnS core/Shell QDs was added to the solution.
(4) The solution was heated at 60° C. with magnetic stirring for 3 hours.
(5) The solution was then cooled down to room temperature.
(6) The QDs were precipitated with excess anhydrous ether, centrifuged at 6000 rpm for 10 minutes, and the supernatant was decanted to remove the organic solvent.
(7) The precipitate was dried up using nitrogen.
(8) The precipitate was then resolved in deionized water.
(9) Finally, the sample was dialyzed overnight, and stored in the dark.

TABLE 8

Transfer of TOPO/ZnS Coated CdSe QDs into Water with Cysteamine.

(1) 0.5 ml (0.65 mg) TOPO-capped CdSe/ZnS core/Shell QDs was removed toluene under vacuum.
(2) 0.5 ml THF was added, mixed.
(3) 50 mg cysteamine hydrochloride was added to a flask, and heated at 80° C.
(4) After melting, QDs in THF was dropped to the flask and heated at 80° C. for 2 hours.
(5) The sample was dried up using nitrogen gas.
(6) Deionized water was added to resolve the sample.
(7) Finally, the sample was dialyzed overnight, and stored in the dark.

The resulting water-soluble QDs can be incorporated into a polymer hydrogel as described herein.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A product comprising:
   an optical sensor;
   a target-responsive hydrogel matrix on a surface of the optical sensor, wherein the hydrogel matrix comprises one or more target-specific receptors and one or more target analogs; and
   one or more high refractive index nanoparticles within the hydrogel matrix;
   wherein a detectable change occurs in a refractive index of the hydrogel matrix when contacted with one or more target molecules.

2. The product according to claim 1, wherein the optical sensor is a porous material.

3. The product according to claim 1, wherein the porous material is a porous semiconductor material comprising p-doped silicon, n-doped silicon, intrinsic or undoped silicon, intrinsic or undoped germanium, doped germanium, a semiconductor material based on a Group II material, a material based on Group III-V materials, a semiconductor material based on a Group VI material, or combinations thereof.

4. The product according to claim 3, wherein the porous semiconductor material is doped with one or more of B, Al, Ga, In, P, As, Sb, and Ge.

5. The product according to claim 3, wherein the porous semiconductor material is silicon.

6. The product according to claim 2, wherein the porous material is selected from the group consisting of single layer materials, double layer architectures, mirrors, microcavities, rugate filters, and stacked combinations of these.

7. The product according to claim 6, wherein the porous material comprises a stack of upper and lower layers including strata of alternating porosity of distinct or graded refractive index, and optionally including a central layer interposed between the upper and lower layers.

8. The product according to claim 2, wherein the porous material is nanoporous, microporous, or macroporous.

9. The product according to claim 2, wherein the porous material is formed from silicon wafers or silicon films on a support.

10. The product according to claim 1, wherein the hydrogel matrix is selected from the group consisting of synthetic hydrogels, natural hydrogels, and mixtures thereof.

11. The product according to claim 10, wherein the hydrogel matrix is selected from the group consisting of polyacrylamide hydrogels, polyvinyl hydrogels, polylactic acid hydrogels, polyglycolic acid hydrogels, polyethylene glycol hydrogels, agarose hydrogels, collagen hydrogels, acrylic hydrogels, acrylated quaternary ammonium monomeric hydrogels, polyurethane hydrogels, organic/inorganic hybrid hydrogels, cross-linked keratin hydrogels, polyethylene amines, chitosan, and combinations thereof.

12. The product according to claim 10, wherein the hydrogel matrix comprises one or more polymers having side groups that can be used to tether bioactive reagents.

13. The product according to claim 1, wherein the hydrogel matrix comprises one or more agents selected from the group consisting of antimicrobial agents, bacteriostatic agents, antiviral agents, and antifungal agents.

14. The product according to claim 1, wherein the one or more receptors and the one or more target analogs form one or more reversible crosslinks within the hydrogel matrix, wherein binding between at least one of the target molecules and at least one of the receptors breaks at least one of the reversible crosslinks, resulting in swelling of the hydrogel matrix and a change in the refractive index of the hydrogel matrix.

15. The product according to claim 14, wherein the one or more high refractive index nanoparticles are nonspecifically encapsulated in the hydrogel matrix, and wherein said swelling of the hydrogel matrix results in release of at least one of the nanoparticles from the hydrogel matrix, whereby a change in the refractive index of the hydrogel matrix occurs.

16. The product according to claim 14, wherein the one or more receptors and/or the one or more target analogs are coupled to the one or more nanoparticles, the one or more receptors, the one or more target analogs, and the one or more nanoparticles collectively forming the one or more reversible crosslinks within the hydrogel matrix, wherein binding between at least one of the target molecules and at least one of the receptors further results in displacement and release of at least one of the nanoparticles from the hydrogel matrix, whereby a change in the refractive index of the hydrogel matrix occurs.

17. The product according to claim 1, wherein the one or more receptors or the one or more target analogs are coupled to the hydrogel matrix and the other of the one or more receptors and the one or more target analogs are coupled to the one or more nanoparticles, whereby the one or more nanoparticles are reversibly bound to the hydrogel matrix, wherein binding between at least one of the target molecules and at least one of the receptors results in displacement and release of at least one of the nanoparticles from the hydrogel matrix, whereby a change in the refractive index of the hydrogel matrix occurs.

18. The product according to claim 1, wherein the one or more receptors are monovalent.

19. The product according to claim 1, wherein the one or more receptors are multivalent.

20. The product according to claim 1, wherein the one or more receptors are selected from the group consisting of non-polymeric small chemical molecule complexes, peptides, polypeptides, proteins, peptide-mimetic compounds, antibody complexes, oligonucleotides, enzymes, and ribozymes.

21. The product according to claim 20, wherein the one or more receptors are selected from the group consisting of receptors for cell surface molecules, lipid A receptors, antibodies or fragments thereof, peptide monobodies, lipopolysaccharide-binding polypeptides, peptidoglycan-binding polypeptides, carbohydrate-binding polypeptides, phosphate-binding polypeptides, nucleic acid-binding polypeptides, and polypeptides that bind an organic warfare agent.

22. The product according to claim 1, wherein the target molecule is selected from the group consisting of antigens, antibodies, proteins, glycoproteins, peptidoglycans, carbohydrates, lipoproteins, lipoteichoic acid, lipid A, phosphates, nucleic acids, pathogens, host markers of infection, organic warfare agents, organic compounds, drugs of abuse, opiates, pain killers, antimicrobial peptides, immune function markers, cancer markers, and disease markers.

23. The product according to claim 1, wherein the one or more high refractive index nanoparticles are selected from the group consisting of InP, PbS, PbSe, CdSe, ZnS, CdSe core ZnS shell, CdTe, CdS, Si, $FeO_y$, $TiO_2$, $Al_xO_y$, $ZnO_s$, SiC, and TiC.

24. The product according to claim 1, wherein the one or more high refractive index nanoparticles have a refractive index greater than 1.5, at least 1.7, greater than 2.0, at least 2.5, or at least 3.6.

25. The product according to claim 1, wherein the one or more high refractive index nanoparticles have a diameter of about 5 to about 50 nm.

26. The product according to claim 2, wherein the one or more high refractive index nanoparticles are small enough to diffuse out of the porous material.

27. The product according to claim 1, wherein the detectable change in the refractive index occurs at a target molecule concentration of between picograms per milliliter and milligrams per milliliter.

28. The product according to claim 27, wherein the detectable change in the refractive index occurs at a target molecule concentration of picograms per milliliter.

29. The product according to claim 27, wherein the detectable change in the refractive index occurs at a target molecule concentration of nanograms per milliliter.

30. The product according to claim 1, wherein the detectable change in the refractive index occurs in the visible range.

31. The product according to claim 1, wherein the detectable change in the refractive index of the hydrogel matrix is amplified by the presence of the high refractive index nanoparticles.

32. The product according to claim 1 further comprising:
a vapor barrier applied to at least one side of the hydrogel matrix.

33. The product according to claim 1 further comprising:
a release layer contacting at least one side of the hydrogel matrix.

34. A sterile package containing a sterile product according to claim 1.

35. A detection device comprising:
a product according to claim 1, and
a source of illumination positioned to illuminate the product.

36. The detection device according to claim 35 further comprising a detector positioned to capture light reflected from the product and to detect changes in the refractive index of the hydrogel matrix.

37. The detection device according to claim 36, wherein the detector is a spectral analyzer of a human eye.

38. A method of detecting a target molecule comprising:
exposing a product according to claim 1 to a sample under conditions effective to allow binding of a target molecule in the sample to the one or more receptors; and
determining whether a change in refractive index of the hydrogel matrix occurs following said exposing, whereby a change in refractive index indicates the presence of the target molecule in the sample.

39. The method according claim 38, wherein said determining comprises:
measuring a first refractive index before said exposing;
measuring a second refractive index after said exposing; and
comparing the first and second refractive indices.

40. The method according to claim 39, wherein said measuring is carried out using a light source and a spectral analyzer.

41. The method according to claim 39, wherein said measuring is carried out using a light source and a spectral analyzer.

42. The method according to claim 38, wherein the sample is blood, water, a suspension of solids in an aqueous solution, or a tissue homogenate.

43. The method according to claim 42, wherein the solids suspended in the aqueous solution are food particles, soil particles, or a cell suspension from a clinical isolate.

44. The method according to claim 38 further comprising:
quantifying the amount of target molecule(s) present in the sample based on the degree of change in refractive index that occurs.

* * * * *